US010612095B2

(12) United States Patent
Treon et al.

(10) Patent No.: US 10,612,095 B2
(45) Date of Patent: *Apr. 7, 2020

(54) METHODS TO DISTINGUISH WALDENSTRÖM'S MACROGLOBULINEMIA FROM IGM MONOCLONAL GAMMOPATHY OF UNDETERMINED SIGNIFICANCE

(71) Applicant: Dana-Farber Cancer Institute, Inc., Boston, MA (US)

(72) Inventors: Steven P. Treon, Jamaica Plain, MA (US); Lian Xu, Waltham, MA (US)

(73) Assignee: Dana-Farber Cancer Institute, Inc., Boston, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/102,034

(22) PCT Filed: Dec. 4, 2014

(86) PCT No.: PCT/US2014/068579
§ 371 (c)(1),
(2) Date: Jun. 6, 2016

(87) PCT Pub. No.: WO2015/085075
PCT Pub. Date: Jun. 11, 2015

(65) Prior Publication Data
US 2016/0304958 A1   Oct. 20, 2016

Related U.S. Application Data

(60) Provisional application No. 61/912,842, filed on Dec. 6, 2013.

(51) Int. Cl.
*C12Q 1/68* (2018.01)
*C12Q 1/6883* (2018.01)
*A61K 31/519* (2006.01)
*A61K 31/5377* (2006.01)
*A61K 31/547* (2006.01)

(52) U.S. Cl.
CPC .......... *C12Q 1/6883* (2013.01); *A61K 31/519* (2013.01); *A61K 31/5377* (2013.01); *A61K 31/547* (2013.01); *C12Q 2600/156* (2013.01)

(58) Field of Classification Search
None
See application file for complete search history.

(56) References Cited

U.S. PATENT DOCUMENTS

| 2004/0137489 A1 | 7/2004 | Shaughnessy |
| 2009/0156469 A1 | 6/2009 | Ghobrial et al. |
| 2010/0009350 A1* | 1/2010 | Chow .................. C12Q 1/6827 435/6.12 |
| 2010/0216115 A1 | 8/2010 | Yan et al. |
| 2012/0065201 A1 | 3/2012 | Honigberg et al. |
| 2012/0071497 A1 | 3/2012 | Buggy et al. |
| 2014/0249142 A1 | 9/2014 | Treon |
| 2016/0222465 A1 | 8/2016 | Treon et al. |
| 2017/0333436 A1 | 11/2017 | Treon et al. |

FOREIGN PATENT DOCUMENTS

| EP | 2 878 601 A1 | 6/2015 |
| WO | WO 2006/067091 A1 | 6/2006 |
| WO | WO 2008/060367 A2 | 5/2008 |
| WO | WO 2013/006443 A2 | 1/2013 |
| WO | WO 2013/071068 A2 | 5/2013 |
| WO | WO 2015/038887 A1 | 3/2015 |

OTHER PUBLICATIONS

Xu et al; Journal of Clinical Oncology, vol. 30, supl. 8042, abstract; May 2012.*
Honigberg et al; PNAS, Jul. 20, 2010vol. 107, pp. 13075-13080.*
Tai et al; Blood, vol. 118, p. 404, Nov. 2011.*
Treon et al; New England Journal of Medicine, vol. 367, pp. 826-833, Aug. 2012.*
Baxter et al; Lancet, vol. 365, pp. 1054-1061, 2005.*
Xu et al; Blood, vol. 121, pp. 2051-2058; Jan. 15, 2013.*
Extended European Search Report for EP14844516.6 dated Mar. 28, 2017.
Tai et al., Targeting Brouton's Tyrosine Kinase with PCI-32765 Blocks Growth and Survival of Multiple Myeloma and Waldenström Macroglobulinemia via Potent Inhibition of Osteoclastogenesis, Cytokines/Chemokine Secretion, and Myeloma Stem-Like Cells in the Bone Marrow Microenvironment. Blood. Nov. 18, 2011;118(21):404.
Extended European Search Report for EP12807230.3 dated Feb. 2, 2015.
Invitation to Pay Additional Fees for PCT/US2012/044956 dated Oct. 1, 2012.
International Search Report and Written Opinion for PCT/US2012/044956 dated Dec. 17, 2012.
International Preliminary Report on Patentability for PCT/US2012/044956 dated Jan. 16, 2014.
International Search Report and Written Opinion for PCT/US2014/055386 dated Dec. 23, 2014.
International Preliminary Report on Patentability for PCT/US2014/055386 dated Mar. 24, 2016.

(Continued)

Primary Examiner — Jehanne S Sitton
(74) Attorney, Agent, or Firm — Wolf, Greenfield & Sacks, P.C.

(57) ABSTRACT

Diagnostic assays for discriminating Waldenstrom's Macroglobulinemia from IgM monoclonal gammopathy of undetermined significance are provided. The method comprises obtaining a biological sample from a subject in need thereof, performing an allele-specific polymerase chain reaction assay to determine in the biological sample a level of a transcript comprising a mutation at position 38182641 in chromosome 3p22.2, and providing a report indicating whether delta $C_T$ value of the biological sample is less than a reference value, wherein the subject has Waldenstrom's Macroglobulinemia if the delta $C_T$ value is less than the reference value.

15 Claims, 2 Drawing Sheets
Specification includes a Sequence Listing.

(56) References Cited

OTHER PUBLICATIONS

International Search Report and Written Opinion for PCT/US2014/068579 dated Mar. 3, 2015.
International Preliminary Report on Patentability for PCT/US2014/068579 dated Jun. 16, 2016.
Advani et al., Bruton tyrosine kinase inhibitor ibrutinib (PCI-32765) has significant activity in patients with relapsed/refractory B-cell malignancies. J Clin Oncol. Jan. 1, 2013;31(1):88-94. doi:10.1200/JCO.2012.42.7906. Epub Oct. 8, 2012.
Anderson et al., Multiple myeloma, version 1.2013. J Natl Compr Canc Netw. Jan. 1, 2013;11(1):11-7.
Arcaini et al., Distinctive clinical and histological features of Waldenström's macroglobulinemia and splenic marginal zone lymphoma. Clin Lymphoma Myeloma Leuk. Feb. 2011;11(1):103-5. doi:10.3816/CLML.2011.n. 020.
Argentou et al., Rapid detection of MYD88-L265P mutation by PCR-RFLP in B-cell lymphoproliferative disorders. Leukemia. Feb. 2014;28(2):447-9. doi: 10.1038/leu.2013.294. Epub Oct. 18, 2013.
Balabanian et al., WHIM syndromes with different genetic anomalies are accounted for by impaired CXCR4 desensitization to CXCL12. Blood. Mar. 15, 2005;105(6):2449-57. Epub Nov. 9, 2004.
Bam et al., Role of Bruton's tyrosine kinase in myeloma cell migration and induction of bone disease. Am J Hematol. Jun. 2013;88(6):463-71. doi: 10.1002/ajh.23433. Epub Mar. 28, 2013.
Berger et al., Clinicopathologic features of Waldenstrom's macroglobulinemia and marginal zone lymphoma: are they distinct or the same entity? Clin Lymphoma. Mar. 2005;5(4):220-4. Abstract.
Bergsagel et al., Comprehensive identification of somatic mutations in chronic lymphocytic leukemia. Cancer Cell. Jul. 12, 2011;20(1):5-7. doi:10.1016/j.ccr.2011.06.023.
Bohers et al., Targetable activating mutations are very frequent in GCB and ABC diffuse large B-cell lymphoma. Genes Chromosomes Cancer. Feb. 2014;53(2):144-53. doi:10.1002/gcc.22126. Epub Nov. 5, 2013.
Brikos et al., Mass spectrometric analysis of the endogenous type I interleukin-1 (IL-1) receptor signaling complex formed after IL-1 binding identifies IL-1RAcP, MyD88, and IRAK-4 as the stable components. Mol Cell Proteomics. Sep. 2007;6(9):1551-9. Epub May 15, 2007.
Busillo et al., Regulation of CXCR4 signaling. Biochim Biophys Acta. Apr. 2007;1768(4):952-63. Epub Nov. 10, 2006.
Busillo et al., Site-specific phosphorylation of CXCR4 is dynamically regulated by multiple kinases and results in differential modulation of CXCR4 signaling. J Biol Chem. Mar. 5, 2010;285(10):7805-17. doi: 10.1074/jbc.M109.091173. Epub Jan. 4, 2010.
Cao et al., CXCR4 WHIM-like frameshift and nonsense mutations promote ibrutinib resistance but do not supplant MYD88(L265P)-directed survival signalling in Waldenström macroglobulinaemia cells. Br J Haematol. Mar. 2015;168(5):701-7. doi: 10.1111/bjh.13200. Epub Nov. 5, 2014.
Cao et al., The WHIM-like CXCR4(S338X) somatic mutation activates AKT and ERK, and promotes resistance to ibrutinib and other agents used in the treatment of Waldenstrom's Macroglobulinemia. Leukemia. Jan. 2015;29(1):169-76. doi: 10.1038/leu.2014.187. Epub Jun. 10, 2014.
Cao et al., Whole Genome Sequencing Identifies Recurring Somatic Mutations in the C-Terminal Domain of CXCR4, Including a Gain of Function Mutation in Waldenstrom's Macroglobinemia. Blood. 2012;120: Abstract 2715.
Carnevali et al., Computational techniques for human genome resequencing using mated gapped reads. J Comput Biol. Mar. 2012;19(3):279-92. doi: 10.1089/cmb.2011.0201. Epub Dec. 16, 2011.
Chen, Treatment for Waldenstrom's macroglobulinemia. Ann Oncol. Apr. 2004;15(4):550-8.
Cheng et al., Binding of Bruton's tyrosine kinase to Fyn, Lyn, or Hck through a Src homology 3 domain-mediated interaction. Proc Natl Acad Sci U S A. Aug. 16, 1994;91(17):8152-5.

Chng et al., Gene-expression profiling of Waldenstrom macroglobulinemia reveals a phenotype more similar to chronic lymphocytic leukemia than multiple myeloma. Blood. Oct. 15, 2006;108(8):2755-63. Epub Jun. 27, 2006.
Davies et al., Preclinical pharmacology of AZD5363, an inhibitor of AKT: pharmacodynamics, antitumor activity, and correlation of monotherapy activity with genetic background. Mol Cancer Ther. Apr. 2012;11(4):873-87. doi: 10.1158/1535-7163.MCT-11-0824-T. Epub Jan. 31, 2012.
Ditzel et al., Establishment of BCWM.1 cell line for Waldenström's macroglobulinemia with productive in vivo engraftment in SCID-hu mice. Exp Hematol. Sep. 2007;35(9):1366-75.
Dotta et al., Clinical and genetic features of Warts, Hypogammaglobulinemia, Infections and Myelokathexis (WHIM) syndrome. Gun Mol Med. Jun. 2011;11(4):317-25.
Drmanac et al., Human genome sequencing using unchained base reads on self-assembling DNA nanoarrays. Science. Jan. 1, 2010;327(5961):78-81.
Evans et al., Inhibition of Btk with CC-292 provides early pharmacodynamic assessment of activity in mice and humans. J Pharmacol Exp Ther. Aug. 2013;346(2):219-28. doi:10.1124/jpet.113.203489. Epub May 24, 2013.
Farré et al., Identification of patterns in biological sequences at the ALGGEN server: PROMO and MALGEN. Nucleic Acids Res. Jul. 1, 2003;31(13):3651-3.
Futahashi et al., Separate elements are required for ligand-dependent and-independent internalization of metastatic potentiator CXCR4. Cancer Sci. Mar. 2007;98(3):373-9.
Gachard et al., IGHV gene features and MYD88 L265P mutation separate the three marginal zone lymphoma entities and Waldenström macroglobulinemia/lymphoplasmacytic lymphomas. Leukemia. Jan. 2013;27(1):183-9. doi: 10.1038/leu.2012.257. Epub Sep. 4, 2012.
Gay et al., Assembly and localization of Toll-like receptor signalling complexes. Nat Rev Immunol. Aug. 2014;14(8):546-58. doi: 10.1038/nri3713.
Genbank Submission; NIH/NCBI, Accession No. NM_001008540. Micucci et al., Mar. 18, 2016.
Gertz et al., Waldenström's macroglobulinemia. Oncologist. 2000;5(1):63-7.
Gopal et al., PI3Kδ inhibition by idelalisib in patients with relapsed indolent lymphoma. N Engl J Med. Mar. 13, 2014;370(11):1008-18. doi: 10.1056/NEJMoa1314583. Epub Jan. 22, 2014.
Gutiérrez et al., Gene expression profiling of B lymphocytes and plasma cells from Waldenström's macroglobulinemia: comparison with expression patterns of the same cell counterparts from chronic lymphocytic leukemia, multiple myeloma and normal individuals. Leukemia. Mar. 2007;21(3):541-9. Epub Jan. 25, 2007.
Hallek et al., Signal transduction of interleukin-6 involves tyrosine phosphorylation of multiple cytosolic proteins and activation of Src-family kinases Fyn, Hck, and Lyn in multiple myeloma cell lines. Exp Hematol. Dec. 1997;25(13):1367-77.
Hanke et al., Discovery of a novel, potent, and Src family-selective tyrosine kinase inhibitor. Study of Lck- and FynT-dependent T cell activation. J Biol Chem. Jan. 12, 1996;271(2):695-701.
Herman et al., Bruton tyrosine kinase represents a promising therapeutic target for treatment of chronic lymphocytic leukemia and is effectively targeted by PCI-32765. Blood. Jun. 9, 2011;117(23):6287-96. doi: 10.1182/blood-2011-01-328484. Epub Mar. 21, 2011.
Hodge et al., IL-21 in the bone marrow microenvironment contributes to IgM secretion and proliferation of malignant cells in Waldenstrom macroglobulinemia. Blood. Nov. 1, 2012;120(18):3774-82. doi: 10.1182/blood-2012-03-419440. Epub Sep. 13, 2012.
Hong et al., The Src family kinase Hck regulates mast cell activation by suppressing an inhibitory Src family kinase Lyn. Blood. Oct. 1, 2007;110(7):2511-9. Epub May 18, 2007. Erratum in: Blood. Mar. 15, 2008;111(6):3299.
Honigberg et al., The Bruton tyrosine kinase inhibitor PCI-32765 blocks B-cell activation and is efficacious in models of autoimmune disease and B-cell malignancy. Proc Natl Acad Sci U S A. Jul. 20, 2010;107(29):13075-80. doi:10.1073/pnas.1004594107. Epub Jul. 6, 2010.

(56) References Cited

OTHER PUBLICATIONS

Hunter et al., Use of whole genome sequencing to identify highly recurrent somatic mutations in Waldenström's macroglobulinemia. 2012 ASCO Annual Meeting. Jun. 1-Jun. 5. Chicago, Illinois: Abstract 8107.

Hunter et al., Recurring activation mutations and somatic deletions revealed through whole genome sequencing in Waldenstrom's Macroglobulinemia. Hematol Oncol. Jun. 2013; 31(S1): Abstract 093.

Hunter et al., The genomic landscape of Waldenstrom macroglobulinemia is characterized by highly recurring MYD88 and WHIM-like CXCR4 mutations, and small somatic deletions associated with B-cell lymphomagenesis. Blood. Mar. 13, 2014;123(11):1637-46. doi:10.1182/blood-2013-09-525808. Epub Dec. 23, 2013.

Janz, Waldenström macroglobulinemia: clinical and immunological aspects, natural history, cell of origin, and emerging mouse models. ISRN Hematol. Sep. 9, 2013;2013:815325. doi: 10.1155/2013/815325.

Jeelall et al., Oncogenic MYD88 mutation drives Toll pathway to lymphoma. Immunol Cell Biol. Aug. 2011;89(6):659-60. doi: 10.1038/icb.2011.31. Epub Apr. 26, 2011.

Jiménez et al., MYD88 L265P is a marker highly characteristic of, but not restricted to, Waldenström's macroglobulinemia. Leukemia. Aug. 2013;27(8):1722-8. doi: 10.1038/leu.2013.62. Epub Feb. 28, 2013.

Jourdan et al., Characterization of a transitional preplasmablast population in the process of human B cell to plasma cell differentiation. J Immunol. Oct. 15, 2011;187(8):3931-41. doi:10.4049/jimmunol.1101230. Epub Sep. 14, 2011.

Juilland et al., CARMA1- and MyD88-dependent activation of Jun/ATF-type AP-1 complexes is a hallmark of ABC diffuse large B-cell lymphomas. Blood. Apr. 7, 2016;127(14):1780-9. doi:10.1182/blood-2015-07-655647. Epub Jan. 8, 2016.

Kawagoe et al., Sequential control of Toll-like receptor-dependent responses by IRAK1 and IRAK2. Nat Immunol. Jun. 2008;9(6):684-91.

Kiss et al., Comparative testing of peripheral blood and bone marrow for BCR-ABL transcripts in patients post allogeneic bone marrow transplantation and during interferon treatment for chronic myeloid leukemia. Leuk Lymphoma. Aug. 1999;34(5-6):493-500.

Kriangkum et al., Clonotypic IgM V/D/J sequence analysis in Waldenstrom macroglobulinemia suggests an unusual B-cell origin and an expansion of polyclonal B cells in peripheral blood. Blood. Oct. 1, 2004;104(7):2134-42. Epub Feb. 5, 2004.

Kyle et al., IgM monoclonal gammopathy of undetermined significance and smoldering Waldenström's macroglobulinemia. Clin Lymphoma Myeloma. Mar. 2009;9(1):17-8.

Kyle et al., Prognostic markers and criteria to initiate therapy in Waldenstrom's macroglobulinemia: consensus panel recommendations from the Second International Workshop on Waldenstrom's Macroglobulinemia. Semin Oncol. Apr. 2003;30(2):116-20.

Kyrtsonis et al., CD138 expression helps distinguishing Waldenström's macroglobulinemia (WM) from splenic marginal zone lymphoma (SMZL). Clin Lymphoma Myeloma Leuk. Feb. 2011;11(1):99-102. doi: 10.3816/CLML.2011.n.019.

Lagane et al., CXCR4 dimerization and beta-arrestin-mediated signaling account for the enhanced chemotaxis to CXCL12 in WHIM syndrome. Blood. Jul. 1, 2008;112(1):34-44. doi: 10.1182/blood-2007-07-102103. Epub Apr. 24, 2008.

Lam et al., Cooperative signaling through the signal transducer and activator of transcription 3 and nuclear factor-{kappa}B pathways in subtypes of diffuse large B-cell lymphoma. Blood. Apr. 1, 2008;111(7):3701-13. Epub Dec. 26, 2007.

Landgren et al., MYD88 L265P somatic mutation in IgM MGUS. N Engl J Med. Dec. 6, 2012;367(23):2255-6; author reply 2256-7. doi: 10.1056/NEJMc1211959#SA1.

Lee et al., The mutation spectrum revealed by paired genome sequences from a lung cancer patient. Nature. May 27, 2010;465(7297):473-7.

Leleu et al., Targeting NF-kappaB in Waldenstrom macroglobulinemia. Blood. May 15, 2008;111(10):5068-77.

Leleu et al., The Akt pathway regulates survival and homing in Waldenstrom macroglobulinemia. Blood. Dec. 15, 2007;110(13):4417-26. Epub Aug. 30, 2007.

Lin et al., Helical assembly in the MyD88-IRAK4-IRAK2 complex in TLR/IL-1R signaling. Nature. Jun. 17, 2010;465(7300):885-90.

Lin et al., Lymphoid neoplasms associated with IgM paraprotein: a study of 382 patients. Am J Clin Pathol. Feb. 2005;123(2):200-5.

Loiarro et al., Identification of critical residues of the MyD88 death domain involved in the recruitment of downstream kinases. J Biol Chem. Oct. 9, 2009;284(41):28093-103.

Loiarro et al., Peptide-mediated interference of TIR domain dimerization in MyD88 inhibits interleukin-1-dependent activation of NF-{kappa}B. J Biol Chem. Apr. 22, 2005;280(16):15809-14. Epub Mar. 8, 2005.

Loiarro et al., Pivotal Advance: Inhibition of MyD88 dimerization and recruitment of IRAK1 and IRAK4 by a novel peptidomimetic compound. J Leukoc Biol. Oct. 2007;82(4):801-10. Epub Jun. 4, 2007.

Martínez et al., Whole-exome sequencing in splenic marginal zone lymphoma reveals mutations in genes involved in marginal zone differentiation. Leukemia. Jun. 2014;28(6):1334-40. doi: 10.1038/leu.2013.365. Epub Dec. 3, 2013.

McDermott et al., A phase 1 clinical trial of long-term, low-dose treatment of WHIM syndrome with the CXCR4 antagonist plerixafor. Blood. Apr. 10, 2014;123(15):2308-16. doi:10.1182/blood-2013-09-527226. Epub Feb. 12, 2014.

McDermott et al., AMD3100 is a potent antagonist at CXCR4 (R334X), a hyperfunctional mutant chemokine receptor and cause of WHIM syndrome. J Cell Mol Med. Oct. 2011;15(10):2071-81. doi: 10.1111/j.1582-4934.2010.01210.x.

McDermott et al., The CXCR4 antagonist plerixafor corrects panleukopenia in patients with WHIM syndrome. Blood. Nov. 3, 2011;118(18):4957-62. doi: 10.1182/blood-2011-07-368084. Epub Sep. 2, 2011.

McMaster et al., Long-term evaluation of three multiple-case Waldenstrom macroglobulinemia families. Clin Cancer Res. Sep. 1, 2007;13(17):5063-9.

Messeguer et al., PROMO: detection of known transcription regulatory elements using species-tailored searches. Bioinformatics. Feb. 2002;18(2):333-4.

Mueller et al., Hierarchical organization of multi-site phosphorylation at the CXCR4 C terminus. PLoS One. May 29, 2013;8(5):e64975. doi: 10.1371/journal.pone.0064975. Print 2013.

Musumeci et al., Hck inhibitors as potential therapeutic agents in cancer and HIV infection. Curr Med Chem. 2015;22(13):1540-64.

Ngo et al., Oncogenically active MYD88 mutations in human lymphoma. Nature. Feb. 3, 2011;470(7332):115-9. doi: 10.1038/nature09671.

Ngo et al., SDF-1/CXCR4 and VLA-4 interaction regulates homing in Waldenstrom macroglobulinemia. Blood. Jul. 1, 2008;112(1):150-8. doi: 10.1182/blood-2007-12-129395. Epub Apr. 30, 2008.

O'Boyle et al., Open Babel: An open chemical toolbox. J Cheminform. Oct. 7, 2011;3:33. doi:10.1186/1758-2946-3-33.

Okuzumi et al., Inhibitor hijacking of Akt activation. Nat Chem Biol. Jul. 2009;5(7):484-93. doi:10.1038/nchembio.183. Epub May 24, 2009.

Ondrejka et al., MYD88 L265P somatic mutation: its usefulness in the differential diagnosis of bone marrow involvement by B-cell lymphoproliferative disorders. Am J Clin Pathol. Sep. 2013;140(3):387-94. doi: 10.1309/AJCP10ZCLFZGYZIP.

Owen et al., Clinicopathological definition of Waldenstrom's macroglobulinemia: consensus panel recommendations from the Second International Workshop on Waldenstrom's Macroglobulinemia. Semin Oncol. Apr. 2003;30(2):110-5.

Passamonti, How I treat polycythemia vera. Blood. Jul. 12, 2012;120(2):275-84. doi: 10.1182/blood-2012-02-366054. Epub May 18, 2012.

Patricelli et al., In situ kinase profiling reveals functionally relevant properties of native kinases. Chem Biol. Jun. 24, 2011;18(6):699-710. doi:10.1016/j.chembiol.2011.04.011.

(56) References Cited

OTHER PUBLICATIONS

Pecquet et al., The Src tyrosine kinase Hck is required for Tel-Abl- but not for Tel-Jak2-induced cell transformation. Oncogene. Mar. 8, 2007;26(11):1577-85. Epub Sep. 4, 2006.
Pene-Dumitrescu et al., An inhibitor-resistant mutant of Hck protects CML cells against the antiproliferative and apoptotic effects of the broad-spectrum Src family kinase inhibitor A-419259. Oncogene. Nov. 27, 2008;27(56):7055-69. doi:10.1038/onc.2008.330. Epub Sep. 15, 2008.
Poh et al., Hematopoietic cell kinase (HCK) as a therapeutic target in immune and cancer cells. Oncotarget. Jun. 30, 2015;6(18):15752-71.
Poulain et al., MYD88 L265P mutation in Waldenstrom macroglobulinemia. Blood. May 30, 2013;121(22):4504-11. doi: 10.1182/blood-2012-06-436329. Epub Mar. 26, 2013.
Powers et al., Discovery and initial SAR of inhibitors of interleukin-1 receptor-associated kinase-4. Bioorg Med Chem Lett. Jun. 1, 2006;16(11):2842-5. Epub Mar. 24, 2006.
Puente et al., Whole-genome sequencing identifies recurrent mutations in chronic lymphocytic leukaemia. Nature. Jun. 5, 2011;475(7354):101-5. doi:10.1038/nature10113.
Roach et al., Analysis of genetic inheritance in a family quartet by whole-genome sequencing. Science. Apr. 30, 2010;328(5978):636-9.
Roccaro et al., A Novel Activating Mutation of CXCR4 Plays a Crucial Role in Waldenstrom Macroglobulinemia Biology. Blood. 2013;122: Abstract 272.
Roccaro et al., C1013G/CXCR4 acts as a driver mutation of tumor progression and modulator of drug resistance in lymphoplasmacytic lymphoma. Blood. Jun. 26, 2014;123(26):4120-31. doi:10.1182/blood-2014-03-564583. Epub Apr. 7, 2014.
Sahota et al., CD27 in defining memory B-cell origins in Waldenström's macroglobulinemia. Clin Lymphoma Myeloma. Mar. 2009;9(1):33-5. doi: 10.3816/CLM.2009.n.007.
Saito et al., A pyrrolo-pyrimidine derivative targets human primary AML stem cells in vivo. Sci Transl Med. Apr. 17, 2013;5(181):181ra52. doi: 10.1126/scitranslmed.3004387.
Sanner et al., Reduced surface: an efficient way to compute molecular surfaces. Biopolymers. Mar. 1996;38(3):305-20.
Schaeffer et al., Signaling through a novel domain of gp130 mediates cell proliferation and activation of Hck and Erk kinases. Mol Cell Biol. Dec. 2001;21(23):8068-81.
Smith et al., In Waldenstrom's macroglobulinemia the quantity of detectable circulating monoclonal B lymphocytes correlates with clinical course. Blood. May 1983;61(5):911-4.
Song et al., The kinase activities of interleukin-1 receptor associated kinase (IRAK)-1 and 4 are redundant in the control of inflammatory cytokine expression in human cells. Mol Immunol. Apr. 2009;46(7):1458-66.
Suh et al., Inhibition of granulocyte-macrophage colony-stimulating factor signaling and microglial proliferation by anti-CD45RO: role of Hck tyrosine kinase and phosphatidylinositol 3-kinase/Akt. J Immunol. Mar. 1, 2005;174(5):2712-9.
Taguchi et al., Characteristic expression of Hck in human B-cell precursors. Exp Hematol. Jan. 2000;28(1):55-64. Erratum in: Exp Hematol. Mar. 2000;28(3):347.
Tai et al., Bruton tyrosine kinase inhibition is a novel therapeutic strategy targeting tumor in the bone marrow microenvironment in multiple myeloma. Blood. Aug. 30, 2012;120(9):1877-87. doi: 10.1182/blood-2011-12-396853. Epub Jun. 11, 2012.
Tiacci et al., Simple genetic diagnosis of hairy cell leukemia by sensitive detection of the BRAF-V600E mutation. Blood. Jan. 5, 2012;119(1):192-5. doi:10.1182/blood-2011-08-371179. Epub Oct. 25, 2011. Erratum in: Blood. Aug. 29, 2013;122(9):1685.
Treon et al., Prospective phase II clinical trial of carfilzomib, rituximab, and dexamethasone (CaRD) in Waldenstrom's macroglobulinemia. 12th International Conference on Malignant Lymphoma. Palazzo dei Congressi, Lugano, Switzerland, Jun. 19-22, 2013, abstract 150, 2013.

Treon et al., A new era for Waldenstrom macroglobulinemia: MYD88 L265P. Blood. May 30, 2013;121(22):4434-6. doi: 10.1182/blood-2013-04-494849.
Treon et al., A Prospective Multicenter Study of the Bruton's Tyrosine Kinase Inhibitor Ibrutinib in Patients With Relapsed or Refractory Waldenstrom's Macroglobulinemia. Blood. 2013;122:Abstract 251.
Treon et al., A prospective, multicenter, phase II study of the Bruton's Tyrosine Kinase Inhibitor Ibrutinib in patients with relapsed and refractory Waldenstrom's Macroglobulinemia. Hematol Oncol. Jun. 2013;31(S1): Abstract 067.
Treon et al., Characterization of familial Waldenstrom's macroglobulinemia. Ann Oncol. Mar. 2006;17(3):488-94. Epub Dec. 15, 2005.
Treon et al., Ibrutinib in previously treated Waldenstrïm's macroglobulinemia. N Engl J Med. Apr. 9, 2015;372(15):1430-40. doi:10.1056/NEJMoa1501548.
Treon et al., Multicenter clinical trial of bortezomib in relapsed/refractory Waldenstrom's macroglobulinemia: results of WMCTG Trial 03-248. Clin Cancer Res. Jun. 1, 2007;13(11):3320-5.
Treon et al., MYD88 L265P somatic mutation in Waldenström's macroglobulinemia. N Engl J Med. Aug. 30, 2012;367(9):826-33. doi:10.1056/NEJMoa1200710.
Treon et al., MYD88 Mutations and Response to Ibrutinib in Waldenström's Macroglobulinemia. N Engl J Med. Aug. 6, 2015;373(6):584-6. doi:10.1056/NEJMc1506192.
Treon et al., Prospective, Multicenter Study of the MTOR Inhibitor Everolimus (RAD001) As Primary Therapy in Waldenstrom's Macroglobulinemia. Blood. 2011;118:Abstract 2951.
Treon et al., Somatic mutations in MYD88 and CXCR4 are determinants of clinical presentation and overall survival in Waldenstrom macroglobulinemia. Blood. May 1, 2014;123(18):2791-6. doi:10.1182/blood-2014-01-550905. Epub Feb. 19, 2014.
Treon et al., Whole Genome sequencing reveals a widely expressed mutation (MYD88 L265P) in Waldenstrom's Macroglobulinemia. Oral and Poster Abstracts. Dec. 2011. 1 Page.
Treon, How I treat Waldenström macroglobulinemia. Blood. Sep. 17, 2009;114(12):2375-85.
Trøen et al., CD79B and MYD88 Mutations in Splenic Marginal Zone Lymphoma. ISRN Oncol. 2013;2013:252318. doi: 10.1155/2013/252318. Epub Jan. 10, 2013.
Trott et al., AutoDock Vina: improving the speed and accuracy of docking with a new scoring function, efficient optimization, and multithreading. J Comput Chem. Jan. 30, 2010;31(2):455-61. doi: 10.1002/jcc.21334.
Varettoni et al., Prevalence and clinical significance of the MYD88 (L265P) somatic mutation in Waldenstrom's macroglobulinemia and related lymphoid neoplasms. Blood. Mar. 28, 2013;121(13):2522-8. doi: 10.1182/blood-2012-09-457101. Epub Jan. 25, 2013.
Wang et al., CD19: a biomarker for B cell development, lymphoma diagnosis and therapy. Experimental Hematol Oncol. 2012;1(36):1-7.
Wang et al., IRAK-4 inhibitors for inflammation. Curr Top Med Chem. 2009;9(8):724-37.
Watters et al., Structure, function and regulation of the Toll/IL-1 receptor adaptor proteins. Immunol Cell Biol. Aug.-Sep. 2007;85(6):411-9. Epub Jul. 31, 2007.
Willenbacher et al., Improved accuracy of discrimination between IgM multiple myeloma and Waldenström macroglobulinaemia by testing for MYD88 L265P mutations. Br J Haematol. Jun. 2013;161(6):902-4. doi:10.1111/bjh.12313. Epub Apr. 5, 2013.
Wilson et al., Targeting B cell receptor signaling with ibrutinib in diffuse large B cell lymphoma. Nat Med. Aug. 2015;21(8):922-6. doi: 10.1038/nm.3884. Epub Jul. 20, 2015.
Woyach et al., Resistance mechanisms for the Bruton's tyrosine kinase inhibitor ibrutinib. N Engl J Med. Jun. 12, 2014;370(24):2286-94. doi: 10.1056/NEJMoa1400029. Epub May 28, 2014.
Xu et al., Detection of MYD88 L265P in Peripheral Blood of Patients With Waldenströ m's Macroglobulinemia and IgM Monoclonal Gammopathy of Undetermined Significance. Blood. 2013;122(21): Abstract 3024.
Xu et al., Detection of MYD88 L265P in peripheral blood of patients with Waldenström's Macroglobulinemia and IgM mono-

(56) References Cited

OTHER PUBLICATIONS clonal gammopathy of undetermined significance. Leukemia. Aug. 2014;28(8):1698-704. doi: 10.1038/leu.2014.65. Epub Feb. 10, 2014.
Xu et al., MYD88 L265P in Waldenström macroglobulinemia, immunoglobulin M monoclonal gammopathy, and other B-cell lymphoproliferative disorders using conventional and quantitative allele-specific polymerase chain reaction. Blood. Mar. 14, 2013;121(11):2051-8. doi: 10.1182/blood-2012-09-454355. Epub Jan. 15, 2013. Erratum in: Blood. Jun. 27, 2013;121(26):5259.
Yang et al., A mutation in MYD88 (L265P) supports the survival of lymphoplasmacytic cells by activation of Bruton tyrosine kinase in Waldenström macroglobulinemia. Blood. Aug. 15, 2013;122(7):1222-32. doi:10.1182/blood-2012-12-475111. Epub Jul. 8, 2013.
Yang et al., Tyrosine kinase inhibition in diffuse large B-cell lymphoma: molecular basis for antitumor activity and drug resistance of dasatinib. Leukemia. Sep. 2008;22(9):1755-66. doi:10.1038/leu.2008.163. Epub Jul. 3, 2008.
Ye et al., t(1;14) and t(11;18) in the differential diagnosis of Waldenstrom's macroglobulinemia. Mod Pathol. Sep. 2004;17(9):1150-4.
EP14844516.6, Mar. 28, 2017, Extended European Search Report.
U.S. Appl. No. 15/581,736, filed Apr. 28, 2017, Pending.
PCT/US2017/030116, Aug. 21, 2017, International Search Report and Written Opinion.
International Search Report and Written Opinion for PCT/US2017/030116 dated Aug. 21, 2017.
Dave et al., Molecular diagnosis of Burkitt's lymphoma. N Engl J Med. Jun. 8, 2006;354(23):2431-42.
Harris et al., A revised European-American classification of lymphoid neoplasms: a proposal from the International Lymphoma Study Group. Blood. Sep. 1, 1994;84(5):1361-92.
Okada et al., Autopsy case of lymphoplasmacytic lymphoma with a large submucosal tumor in the stomach. Pathol Int. Oct. 2001;51(10):802-6.
Yang et al., HCK Is a Highly Relevant Target of Ibrutinib in MYD88 Mutated Waldenstrom's Macroglobulinemia and Diffuse Large B-Cell Lymphoma. Blood. 2015;126:705.
U.S. Appl. No. 15/581,736, filed Apr. 28, 2017, Published, 2017-0333436.
[No Author Listed] Package Insert. Campath (Alemtuzumab). Millennium and ILEX Partners, LP. Date created Sep. 26, 2003;1-11.
[No Author Listed] Trademark Electronic Search System (TESS) Typed Drawing. May 21, 1991. 2nd Renewal Apr. 24, 2013. Last accessed Apr. 4, 2018.
Dasmahaptra et al., The Bruton tyrosine kinase (BTK) inhibitor PCI-32765 synergistically increases proteasome inhibitor activity in diffuse large-B cell lymphoma (DLBCL) and mantle cell lymphoma (MCL) cells sensitive or resistant to bortezomib. Br J. Haematol. Apr. 2013;161(1):4356. Abstract only.
International Preliminary Report on Patentability for PCT/US2017/030116 dated Jun. 16, 2016.

\* cited by examiner

METHODS TO DISTINGUISH WALDENSTRÖM'S MACROGLOBULINEMIA FROM IGM MONOCLONAL GAMMOPATHY OF UNDETERMINED SIGNIFICANCE

RELATED APPLICATIONS

This application is a national stage filing under 35 U.S.C. § 371 of International Application No. PCT/US2014/068579, filed Dec. 4, 2014, and entitled "METHODS TO DISTINGUISH WALDENSTROM'S MACROGLOBULINEMIA FROM IGM MONOCLONAL GAMMOPATHY OF UNDETERMINED SIGNIFICANCE," which claims the benefit under 35 U.S.C. § 119(e) of U.S. provisional application Ser. No. 61/912,842, filed Dec. 6, 2013, the entire contents of which are incorporated by reference herein in their entirety.

BACKGROUND OF THE INVENTION

Waldenström's macroglobulinemia (WM) is a distinct clinicopathological entity resulting from the accumulation, predominantly in the bone marrow, of clonally related lymphoplasmacytic cells which secrete a monoclonal IgM protein. This condition is considered to correspond to lymphoplasmacytic lymphoma (LPL) as defined by the World Health Organization classification system. Genetic factors play an important role in the pathogenesis of WM, with 25% of patients demonstrating a family history. IgM monoclonal gammopathy of unknown significance (IgM MGUS) often precedes the development of WM. It is clinically difficult to distinguish WM from IgM MGUS, which may have a similar immunophenotype on examination of neoplastic cells but differs greatly in prevalence and prognosis. Thus, methods to better discriminate WM from IgM MGUS are needed to permit advances in diagnostic testing, and development of targeted therapies.

SUMMARY OF THE INVENTION

It has been discovered, surprisingly, that delta $C_T$ values of a somatic mutation in the myeloid differentiation primary response (MYD88) gene determined using quantitative allele-specific polymerase chain reaction is lower in Waldenström's macroglobulinemia patients than in IgM monoclonal gammopathy of unknown significance patients. Thus, the present application provides convenient methods to discriminate WM from IgM MGUS based on the delta $C_T$ value for the mutant MYD88 gene.

Accordingly, in some aspects, the present invention involves a method to distinguish Waldenström's Macroglobulinemia from IgM monoclonal gammopathy of undetermined significance in a subject. The method, comprises obtaining a biological sample from a subject in need thereof, performing an allele-specific polymerase chain reaction assay to determine in the biological sample a level of a transcript comprising a mutation at position 38182641 in chromosome 3p22.2, and providing a report indicating whether delta CT value of the biological sample is less than a reference value, wherein the subject is more likely to have Waldenström's Macroglobulinemia than IgM monoclonal gammopathy of undetermined significance if the delta CT value is less than the reference value.

In some embodiments, the biological sample is a sample of bone marrow, lymph node, spleen or blood. In some embodiments, the mutation results in a single nucleotide change from T to C in the myeloid differentiation primary response 88 (MYD88) gene. In some embodiments, the mutation results in an amino acid change from leucine to proline at position 265 in the myeloid differentiation primary response 88 protein. In some embodiments, the allele specific polymerase chain reaction assay is performed using an allele specific primer, wherein the allele specific primer hybridizes at or near its 3' end to the mutation at position 38182641 in chromosome 3p22.2. In some embodiments, the allele specific primer is SEQ ID NO: 1.

According to one aspect of the invention, a method to treat Waldenström's Macroglobulinemia in a subject is provided. The method comprises performing an allele-specific polymerase chain reaction assay to determine a level of a transcript comprising a mutation at position 38182641 in chromosome 3p22.2 in a biological sample obtained from a subject in need thereof, and administering to the subject a therapeutic agent in an amount effective to treat Waldenström's Macroglobulinemia if delta CT value of the biological sample is less than a reference value.

In some embodiments, the biological sample is a sample of bone marrow, lymph node, spleen or blood. In some embodiments, the mutation results in a single nucleotide change from T to C in the myeloid differentiation primary response 88 (MYD88) gene. In some embodiments, the mutation results in an amino acid change from leucine to proline at position 265 in the myeloid differentiation primary response 88 protein. In some embodiments, the therapeutic agent is a MYD88 inhibitor, an interleukin receptor associate kinase 1/4 (IRAK-1/4) inhibitor, a phosphoinositide 3-kinase (PI3K) inhibitor and/or a Bruton's tyrosine kinase (BTK) inhibitor. In some embodiments, the MYD88 inhibitor is a peptidomimetic compound ST2825. In some embodiments, the IRAK-1/4 inhibitor is N-(2-Morpholinylethyl)-2-(3-nitrobenzoylamido)-benzimidazole. In some embodiments,the BTK inhibitor is Ibrutinib (PCI-32765).

According to one aspect of the invention, a method to distinguish Waldenström's Macroglobulinemia from IgM monoclonal gammopathy of undetermined significance is provided. The method comprises selecting a subject on the basis that the subject presents one or more of clinical features of WM and/or IgM MGUS, obtaining a biological sample from the subject, performing an allele-specific polymerase chain reaction assay to determine in the biological sample a level of a transcript comprising a mutation at position 38182641 in chromosome 3p22.2, and providing a report indicating whether delta CT value of the biological sample is less than a reference value, wherein the subject is more likely to have Waldenström's Macroglobulinemia than IgM monoclonal gammopathy of undetermined significance if the delta CT value is less than the reference value.

In some embodiments, the biological sample is a sample of bone marrow, lymph node, spleen or blood. In some embodiments, the mutation results in a single nucleotide change from T to C in the myeloid differentiation primary response 88 (MYD88) gene. In some embodiments, the mutation results in an amino acid change from leucine to proline at position 265 in the myeloid differentiation primary response 88 protein. In some embodiments, the allele specific polymerase chain reaction assay is performed using an allele specific primer, wherein the allele specific primer hybridizes at or near its 3' end to the mutation at position 38182641 in chromosome 3p22.2. In some embodiments, the allele specific primer is SEQ ID NO: 1.

According to one aspect of the invention, a method to distinguish Waldenström's Macroglobulinemia from IgM monoclonal gammopathy of undetermined significance is provided. The method comprises performing an assay to determine if the subject has an abnormal level of immunoglobulin M (IgM) in a biological sample obtained from a subject, and performing an allele-specific polymerase chain reaction assay to determine a level of a transcript comprising a mutation at position 38182641 in chromosome 3p22.2 in a biological sample obtained from a subject, wherein the subject is more likely to have Waldenström's Macroglobulinemia than IgM monoclonal gammopathy of undetermined significance if the subject has an abnormal level of IgM and delta CT value of the biological sample is less than a reference value.

In some embodiments, the biological sample used to determine if the subject has an abnormal level of IgM is a sample of blood, urine, bone marrow, lymph node, or spleen. In some embodiments, the biological sample used to determine the level of a transcript comprising a mutation at position 38182641 in chromosome 3p22.2 is a sample of blood, bone marrow, lymph node, or spleen. In some embodiments, the mutation results in a single nucleotide change from T to C in the myeloid differentiation primary response 88 (MYD88) gene. In some embodiments, the mutation results in an amino acid change from leucine to proline at position 265 in the myeloid differentiation primary response 88 protein. In some embodiments, the allele specific polymerase chain reaction assay is performed using an allele specific primer, wherein the allele specific primer hybridizes at or near its 3' end to the mutation at position 38182641 in chromosome 3p22.2. In some embodiments, the allele specific primer is SEQ ID NO: 1.

These and other aspects of the inventions, as well as various advantages and utilities will be apparent with reference to the Detailed Description. Each aspect of the invention can encompass various embodiments as will be understood.

BRIEF DESCRIPTION OF THE DRAWINGS

FIG. 2 shows the real-time AS-PCR results for paired BM and PB MYD88 L265P in patients with WM and IgM MGUS.

DETAILED DESCRIPTION OF THE INVENTION

Figure 1:
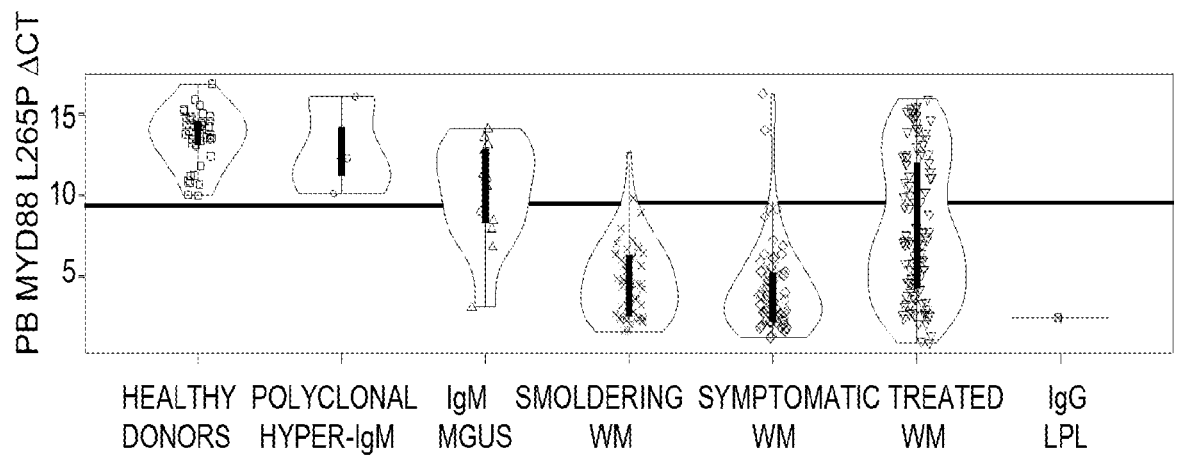
FIG. 1 shows real-time AS-PCR results for PB MYD88 L265P in patients with WM, IgM MGUS, other B-cell disorders, and healthy donors. Violin plots representing AS-PCR differences in cycle threshold (ΔCt). The span of grey area for each cohort represents the kernel density estimation of the sample distribution, and highlights the bimodal nature of the data. Box plots with interquartile ranges are shown in black with an overlay of the individual data points. Samples evaluated were from healthy donors (n=40) or patients with polyclonal hyper-IgM (n=3), IgM MGUS (n=12); smoldering WM (n=51); symptomatic WM (n=67); previously treated WM (n=108); and IgG LPL (n=1). The light grey bar represents the distance between the highest positive, and lowest negative ΔCt values.

A somatic mutation in the myeloid differentiation primary response (MYD88) gene has been previously identified in patients with Waldenström's macroglobulinemia (WM). The mutation results in a single nucleotide change from T→C in the MYD88 gene at position 38182641 in chromosome 3p22.2, and a predicted non-synonymous change at amino acid position 265 from leucine to proline (MYD88 L265P), and has been identified as the most prevalent somatic gene mutation in WM. While a previous study attempted to differentiate WM from IgM monoclonal gammopathy of unknown significance (IgM MGUS) based on the presence or absence of this mutation (WO 2013/006443), subsequent studies demonstrated that 50-80% of IgM monoclonal gammopathy of unknown significance (IgM MGUS) patients were also shown to express the mutation MYD88 L265P (Landgren O, Staudt L: MYD88 L265P somatic mutation in IgM MGUS. N Engl J Med 2012; 367:2255-6; Jimenez C, Sebastian E, Del Carmen Chillon M, et al: MYD88 L265P is a marker highly characteristic of, but not restricted to, Waldenstrom's macroglobulinemia. Leukemia 2013; August; 27(8):1722-8). Thus, the presence of the mutation in both WM and IgM MGUS patients hampers the differential diagnosis of these two diseases.

The present invention is based on the surprising discovery that delta $C_T$ value for the mutant MYD88 L265P identified using quantitative allele-specific polymerase chain reaction (AS-PCR) assay is lower in WM patients than in IgM MGUS patients. Thus, the present application provides a convenient method to discriminate WM from IgM MGUS based on the delta $C_T$ value for the mutant MYD88 L265P.

According to one aspect, the present invention provides a method to distinguish WM from IgM MGUS in a subject, the method comprising obtaining a biological sample from a subject in need thereof, performing an allele-specific polymerase chain reaction assay to determine in the biological sample a level of a transcript comprising a mutation at position 38182641 in chromosome 3p22.2, providing a report indicating whether delta CT value of the biological sample is less than a reference value, wherein the subject is more likely to have Waldenström's Macroglobulinemia than IgM monoclonal gammopathy of undetermined significance if the delta $C_T$ value is less than a reference value.

WM is a B-cell neoplasm categorized as an IgM secreting lymphoplasmacytic lymphoma (LPL) by the WHO classification system. The disease is primarily characterized by bone marrow (BM) infiltration with lymphoplasmacytic cells (LPC), though up to 20% of patients can exhibit extramedullary disease. Circulating WM cells identified by flow cytometry or clonotypic IgM V/D/J rearrangements are present in WM patients, and parallel disease burden. At present, the diagnosis of WM is contingent on demonstrating a LPC infiltrate, most typically by BM biopsy which can produce patient discomfort, result in unforeseen complications, represent a significant burden of cost, as well as delay the diagnosis of WM.

IgM Monoclonal gammopathy of undetermined significance (IgM MGUS) is an asymptomatic premalignant clonal plasma cell or lymphoplasmacytic proliferative disorder. This condition is clinically significant because of the high likelihood that in some patients IgM MGUS will progress to lymphoma or Waldenström's macroglobulinemia.

Because a diagnosis is rarely based exclusively on the results of a single test, the methods described herein may be used to determine whether a subject is more likely to have WM than IgM MGUS, based on the delta $C_T$ value for the mutant MYD88 L265P. Thus, for example, a subject may be diagnosed as being "more likely" or "less likely" to have WM than IgM MGUS in light of the information provided by a method of the present invention. In some embodiments, the methods described herein may be used in conjunction with other diagnostic tests, such as but not limited to, bone marrow biopsies and blood tests, to help confirm the diagnosis. In some embodiments, the methods described herein are used to determine if the subject has WM. Alternatively, the methods described herein are used to rule out a diagnosis of IgM MGUS. And likewise, the methods described herein may be used to determine whether a subject is more likely to have IgM MGUS than WM, based on the delta $C_T$ value for the mutant MYD88 L265P. In some embodiments, the methods described herein are used to determine if the subject has IgM MGUS. Alternatively, the methods described herein are used to rule out a diagnosis of WM.

The term "mutation" means any change or difference in the nucleic acid or protein sequence of MYD88 as compared to the wild type sequence that results in the activation of MYD88 which leads to the activation of NF-κB. Mutations may be identified by comparing the sequence of a subject to that of a wildtype individual or to reference sequences found in the public databases. Mutations include, but are not limited to, nonsense mutations, missense mutations, frameshift mutations, rearrangement mutations, insertion mutations and deletion mutations. In some embodiments, the mutation is a somatic mutation at position 38182641 in chromosome 3p22.2 which results in a single nucleotide change from T→C in the myeloid differentiation primary response (MYD88) gene, and a predicted non-synonymous change at amino acid position 265 from leucine to proline (L265P).

As used herein, a transcript comprising a mutation means MYD88 nucleic acid that has a mutation at position 38182641 in chromosome 3p22.2. In normal (healthy) subjects the mutation is absent. Although it is believed that most of the transcription of the MYD88 gene occurs in the bone marrow, levels of the transcript and protein will be present in the circulation because of the normal turnover and presence of dead cells in the blood.

In some embodiments, the level of the transcript comprising a mutation at position 38182641 in chromosome 3p22.2 is determined by allele specific polymerase chain reaction (AS-PCR). Quantitative AS-PCR for MYD88-L265P may be performed as described in Xu et al. (Blood. 2013 Mar. 14; 121(11):2051-8) and in WO 2013/006443, the contents of each of which are incorporated herein by reference. Allele specific primers are used which hybridize at or near their 3' ends to a particular mutation in the MYD88 gene. If the mutation is not present, the 3'-terminal mismatched primer does not initiate replication, and an amplification product is not observed. In some embodiments, only the forward primer or the reverse primer hybridizes at or near its 3' ends to a particular mutation in the MYD88 gene. In some embodiments, both the forward and the reverse primer hybridize at or near their 3' ends to a particular mutation in the MYD88 gene. In some embodiments, the allele specific primer is SEQ ID NO: 1. In some embodiments, the mutation is a somatic mutation at position 38182641 in chromosome 3p22.2 which results in a single nucleotide change from T→C in the myeloid differentiation primary response (MYD88) gene, and a predicted non-synonymous change at amino acid position 265 from leucine to proline (L265P).

Levels of the transcript comprising a mutation at position 38182641 in chromosome 3p22.2 in patient samples can be calculated based on the value of delta $C_T$ determined using AS-PCR. As used herein, $C_T$ or threshold cycle refers to the PCR cycle number at which the reporter fluorescence crosses a threshold set by the user. As used herein, "delta $C_T$", also called "ΔCt" refers to the difference between the threshold cycle of the mutant and the wild type at the selected threshold. If the delta $C_T$ is less than a reference value, the subject is diagnosed as having WM.

A reference value, as used herein, represents the delta $C_T$ cutoff value that can differentiate between subjects with WM and IgM MGUS, and may vary depending on the assay conditions, and the primers used. A reference value can be identified by determining the MYD88 L265P delta $C_T$ value in subjects known to have WM and the MYD88 L265P delta $C_T$ value in subjects known to have IgM MGUS. A reference value is then selected such that all subjects with WM have a delta $C_T$ value that is less than the selected reference value and all subjects with IgM MGUS have a delta $C_T$ value that is higher than the selected reference value. In some embodiments, a reference value represents a delta $C_T$ value such that 50%, 60%, 70%, 80%, 85%, 90%, 95% or 99% of the subjects with WM have a delta $C_T$ value that is less than the selected reference value, while 50%, 60%, 70%, 80%, 85%, 90%, 95% or 99% of the subjects with IgM MGUS have a delta Ct value that is more than the selected reference value. For the sake of completeness and avoidance of doubt, the present invention covers any one of the above mentioned percentage values for WM and any one of the above mentioned percentage values for IgM MGUS. For example, a reference value may represent a delta $C_T$ value such that 85% of the subjects with WM have a delta $C_T$ value that is less than the selected reference value, and 60% of the subjects with IgM MGUS have a delta Ct value that is more than the selected reference value. In some embodiments, 90% of the subjects with WM have a delta $C_T$ value that is less than the selected reference value, and 90% of the subjects with IgM MGUS have a delta Ct value that is more than the selected reference value. In some embodiments, 95% of the subjects with WM have a delta $C_T$ value that is less than the selected reference value, and 100% of the subjects with IgM MGUS have a delta Ct value that is more than the selected reference value. In some embodiments, 100% of the subjects with WM have a delta $C_T$ value that is less than the selected reference value, and 80% of the subjects with IgM MGUS have a delta Ct value that is more than the selected reference value.

In some embodiments, the reference value is about 3.0, 3.5, 4.0, 4.5, 5.0, 5.5, 6.0, 6.5, 7.0, 7.5, 8.0, 8.5, 9, 9.5 or 10. In some embodiments, the reference value is 3.0, 3.5, 4.0, 4.5, 5.0, 5.5, 6.0, 6.5, 7.0, 7.5, 8.0, 8.5, 9, 9.5 or 10. In some embodiments, the reference value is about 6.5. In some embodiments, the reference value is 6.5.

As used herein, a "subject in need thereof" is a subject suspected of having WM or IgM MGUS. Thus, the subject presents one or more clinical features of WM and/or IgM MGUS. The one or more clinical features of WM include anemia, hyper-viscosity, neuropathy, coagulopathies, splenomegaly, hepatomegaly, adenopathy, an elevated serum IgM levels and the presence of an IgM monoclonal protein. The one or more clinical features of IgM MGUS include monoclonal paraprotein band lesser than 30 g/L (<3 g/dL), plasma cells less than 10% on bone marrow examination, no evidence of bone lesions, anemia, hypercalcemia, or renal insufficiency related to the paraprotein, and no evidence of another B-cell proliferative disorder. In some embodiments, a subject in need thereof presents two or more, three or more, four or more, five or more, six or more, or seven or more of the above described clinical features of WM and/or IgM MGUS.

The subject (individual) is a mammal. In some embodiments, the subject is a human.

Non-limiting examples of the biological sample include bone marrow, lymph node, spleen or blood. In some embodiments, the biological sample is blood. Obtaining a biological sample from a subject means taking possession of a biological sample of the subject. In some embodiments, the biological sample may be removed from the subject by a medical practitioner (e.g., a doctor, nurse, or a clinical laboratory practitioner), and then provided to the person determining the presence of the mutation. The biological sample may be provided to the person determining the mutation by the subject or by a medical practitioner (e.g., a doctor, nurse, or a clinical laboratory practitioner). In some embodiments, the person determining the mutation obtains a biological sample from the subject by removing the sample from the subject.

A report summarizing the results of the analysis, i.e. delta $C_T$ of the mutation and any other information pertaining to the analysis could optionally be generated as part of the analysis (which may be interchangeably referred to herein as "providing" a report, "producing" a report, or "generating" a report). Examples of reports may include, but are not limited to, reports in paper (such as computer-generated printouts of test results) or equivalent formats and reports stored on computer readable medium (such as a CD, computer hard drive, or computer network server, etc.). Reports, particularly those stored on computer readable medium, can be part of a database (such as a database of patient records, which may be a "secure database" that has security features that limit access to the report, such as to allow only the patient and the patient's medical practitioners to view the report, for example). In addition to, or as an alternative to, generating a tangible report, reports can also be displayed on a computer screen (or the display of another electronic device or instrument).

A report can further be transmitted, communicated or reported (these terms may be used herein interchangeably), such as to the individual who was tested, a medical practitioner (e.g., a doctor, nurse, clinical laboratory practitioner, genetic counselor, etc.), a healthcare organization, a clinical laboratory, and/or any other party intended to view or possess the report. The act of 'transmitting' or 'communicating' a report can be by any means known in the art, based on the form of the report, and includes both oral and non-oral transmission. Furthermore, "transmitting" or "communicating" a report can include delivering a report ("pushing") and/or retrieving ("pulling") a report. For example, non-oral reports can be transmitted/communicated by such means as being physically transferred between parties (such as for reports in paper format), such as by being physically delivered from one party to another, or by being transmitted electronically or in signal form (e.g., via e-mail or over the internet, by facsimile, and/or by any wired or wireless communication methods known in the art), such as by being retrieved from a database stored on a computer network server, etc.

According to one aspect of the invention, a method to distinguish Waldenström's Macroglobulinemia from IgM monoclonal gammopathy of undetermined significance, is provided, the method comprising selecting a subject on the basis that the subject presents one or more clinical features of WM and/or IgM MGUS, obtaining a biological sample from the subject, performing an allele-specific polymerase chain reaction assay to determine in the biological sample a level of a transcript comprising a mutation at position 38182641 in chromosome 3p22.2, and providing a report indicating whether delta CT value of the biological sample is less than a reference value, wherein the subject is more likely to have Waldenström's Macroglobulinemia than IgM monoclonal gammopathy of undetermined significance if the delta CT value is less than the reference value.

As used herein, "selecting a subject" means identifying a subject that presents one or more clinical features of WM and/or IgM MGUS for further diagnostic analysis. The one or more clinical features of WM include anemia, hyperviscosity, neuropathy, coagulopathies, splenomegaly, hepatomegaly, adenopathy, and an IgM serum paraprotein. The one or more clinical features of IgM MGUS include monoclonal paraprotein band lesser than 30 g/L (<3 g/dL), plasma cells less than 10% on bone marrow examination, no evidence of bone lesions, anemia, hypercalcemia, or renal insufficiency related to the paraprotein, and no evidence of another B-cell proliferative disorder. In some embodiments, a subject presenting two or more, three or more, four or more, five or more, six or more, or seven or more of the above described clinical features of WM and/or IgM MGUS is selected. The subject is selected by a medical practitioner (e.g., a doctor, nurse, clinical laboratory practitioner, genetic counselor, etc.), a healthcare organization, or a clinical laboratory.

According to one aspect of the invention, a method to distinguish Waldenström's Macroglobulinemia from IgM monoclonal gammopathy of undetermined significance is provided, the method comprising performing an assay to determine if the subject has an abnormal level of immunoglobulin M (IgM) in a biological sample obtained from a subject, and performing an allele-specific polymerase chain reaction assay to determine a level of a transcript comprising a mutation at position 38182641 in chromosome 3p22.2 in a biological sample obtained from a subject, wherein the subject is more likely to have Waldenström's Macroglobulinemia than IgM monoclonal gammopathy of undetermined significance if the subject has an abnormal level of IgM and delta CT value of the biological sample is less than a reference value.

Assays to determine whether a subject has an abnormal level of IgM are well known in the art. For example, O'Connell et al. (*Understanding and Interpreting Serum Protein Electrophoresis*, Am Fam Physician. 2005 Jan. 1; 71(1):105-112; the contents of which are incorporated herein in their entirety) describes the serum protein electrophoresis test that is used to identify subjects having abnormal serum proteins. Another test, such as immunofixation or immunoelectrophoresis, can also be used to determine the type of antibody that is abnormal (IgM or some other type) (Bossuyt et al. *Serum protein electrophoresis and immunofixation by a semiautomated electrophoresis system*. Clinical Chemistry May 1998 vol. 44 no. 5 944-949, the contents of which are incorporated herein in their entirety). As used herein, an abnormal level of IgM refers to a level that is higher than the level found in normal (healthy) subject. Typically, normal serum IgM levels in adults are in the range of 45 to 250 mg/dL. In some embodiments, levels of serum IgM greater than 500 mg/dl, 1 g/dl, 1.5 g/dL, 2 g/dl, 2.5 g/dl, 3 g/dl, or 3.5 g/dL are considered to be abnormal, and indicate a diagnosis of WM, rather than IgM MGUS. In some embodiments, levels of serum IgM greater than 2 g/dL are considered to be abnormal. In some embodiments, levels of serum IgM greater than 3 g/dL are considered to be abnormal.

Non-limiting examples of biological samples used to determine if the subject has an abnormal level of IgM include blood, urine, bone marrow, lymph node, or spleen. Non-limiting examples of biological samples used to determine the level of a transcript comprising a mutation at position 38182641 in chromosome 3p22.2 include blood, bone marrow, lymph node, or spleen. In some embodiments, two distinct biological samples are obtained from the subject to perform the assays to determine if the subject has an abnormal level of IgM and to determine the level of a transcript comprising a mutation at position 38182641 in chromosome 3p22.2. In some embodiments, a single biological sample is obtained from the subject and is used to determine both if the subject has an abnormal level of IgM and the level of a transcript comprising a mutation at position 38182641 in chromosome 3p22.2. The subject is diagnosed as being more likely to have WM than IgM MGUS if the subject has an abnormal level of IgM and delta $C_T$ value of the biological sample is less than a reference value.

According to one aspect of the invention, methods to treat Waldenström's Macroglobulinemia in a subject are provided. The methods comprise performing an allele-specific polymerase chain reaction assay to determine a level of a transcript comprising a mutation at position 38182641 in chromosome 3p22.2 in a biological sample obtained from a subject in need thereof, and administering to the subject a therapeutic agent in an amount effective to treat Waldenström's Macroglobulinemia if delta $C_T$ value of the biological sample is less than a reference value.

The therapeutic agent can be any agent known to be useful in the treatment of WM. Examples of therapeutic agents include, but at not limited to, myeloid differentiation primary response 88 (MYD88) inhibitors, interleukin receptor associate kinase 1/4 (IRAK-1/4) inhibitors, a phosphoinositide 3-kinase (PI3K) inhibitor and/or a Bruton's tyrosine kinase (BTK) inhibitors. Several examples of these kinase inhibitors are known and described in the art. A non-limiting example of an MYD88 inhibitor includes the peptidomimetic compound ST2825 (WO 2006/06709). A non-limiting example of an IRAK-1/4 inhibitor is N-(2-Morpholinyl-ethyl)-2-(3-nitrobenzoylamido)-benzimidazole. In some embodiments, BTK inhibitors useful in the instant invention block MYD88 L265P and BTK signaling. A non-limiting example of a BTK inhibitor includes Ibrutinib (PCI-32765). Non-limiting examples of PI3K inhibitors are described in WO 2013/052699.

The therapeutic agent is administered in an effective amount. An effective amount is a dose sufficient to provide a medically desirable result and can be determined by one of skill in the art using routine methods. In some embodiments, an effective amount is an amount which results in any improvement in the condition being treated. In some embodiments, an effective amount may depend on the extent of WM being treated and/or use of one or more additional therapeutic agents. However, one of skill in the art can determine appropriate doses and ranges of therapeutic agents to use, for example based on in vitro and/or in vivo testing and/or other knowledge of compound dosages.

When administered to a subject, effective amounts of the therapeutic agent will depend, of course, on the particular disease being treated; the severity of the disease; individual patient parameters including age, physical condition, size and weight, concurrent treatment, frequency of treatment, and the mode of administration. These factors are well known to those of ordinary skill in the art and can be addressed with no more than routine experimentation. In some embodiments, a maximum dose is used, that is, the highest safe dose according to sound medical judgment.

In the treatment of WM, an effective amount is that amount which slows the progression of the disease, halts the progression of the disease, or reverses the progression of the disease. An effective amount includes, but is not limited to, that amount necessary to slow, reduce, inhibit, ameliorate or reverse one or more symptoms associated with WM. In some embodiments, such terms refer to a reduction in the levels of IgM serum paraprotein, anemia, hyper-viscosity, neuropathy, coagulopathies, splenomegaly, hepatomegaly, and adenopathy.

An effective amount of a compound typically will vary from about 0.001 mg/kg to about 1000 mg/kg in one or more dose administrations, for one or several days (depending of course of the mode of administration and the factors discussed above).

Actual dosage levels of the therapeutic agent can be varied to obtain an amount that is effective to achieve the desired therapeutic response for a particular patient, compositions, and mode of administration. The selected dosage level depends upon the activity of the particular compound, the route of administration, the tissue being treated, and prior medical history of the patient being treated. However, it is within the skill of the art to start doses of the compound at levels lower than required to achieve the desired therapeutic effort and to gradually increase the dosage until the desired effect is achieved.

Pharmaceutical preparations and compounds comprising the therapeutic agents such as MYD88 inhibitor, IRAK-1/4 inhibitor, and/or BTK inhibitor are administered to a subject by any suitable route. For example, compositions can be administered orally, including sublingually, rectally, parenterally, intracisternally, intravaginally, intraperitoneally, topically and transdermally (as by powders, ointments, or drops), bucally, or nasally. The pharmaceutical preparations of the present invention may include or be diluted into a pharmaceutically-acceptable carrier. The term "pharmaceutically-acceptable carrier" as used herein means one or more compatible fillers, diluents or other such substances, which are suitable for administration to a human or other mammal such as a dog, cat, or horse. The term "carrier" denotes an organic or inorganic ingredient, natural or synthetic, with which the active ingredient is combined to facilitate the application. The carriers are capable of being commingled with the preparations of the present invention, and with each other, in a manner such that there is no interaction which would substantially impair the desired pharmaceutical efficacy or stability. Carriers suitable for oral, subcutaneous, intravenous, intramuscular, etc. formulations can be found in Remington's Pharmaceutical Sciences, Mack Publishing Company, Easton, Pa.

The present invention is further illustrated by the following Example, which in no way should be construed as further limiting. The entire contents of all of the references (including literature references, issued patents, published patent applications, and co-pending patent applications) cited throughout this application are hereby expressly incorporated by reference.

EXAMPLES

Example 1

Materials and Methods

Peripheral blood (PB) was collected from 230 patients with WM, including 118 untreated patients with smoldering (n=51) and symptomatic (n=67) disease; 102 with previously treated disease, 12 individuals with IgM MGUS, 3 with polyclonal hyper-IgM, 1 with IgG LPL, and 40 healthy donors. WM and IgM MGUS patients met consensus criteria for diagnosis, and symptomatic patients met consensus criteria for initiation of therapy.1,24 Sixty-one untreated WM, 66 previously treated WM, 12 IgM MGUS, 3 polyclonal hyper-IgM syndrome and 1 IgG LPL untreated patients had paired PB and BM samples. The clinical characteristics for all and paired WM and IgM MGUS patients are provided in Table 1.

CD19-selected cells from BM aspirates were isolated as previously reported.7,9 CD19-cells from PB samples were isolated using CD19 Dynabeads Pan B Kit (Life Technologies, Carlsbad, Calif.). For this assay, 8 ml of PB and 200 ul of Dynabeads were mixed and incubated for 20 min at 4 oC with gentle rotation. The beads were magnetically collected and washed thrice with isolation buffer. 350 ul of RLTplus cell lysis buffer (AllPrep DNA/RNA Mini Kit, Qiagen) was added to the beads and DNA was extracted according to manufacturer's protocol (Qiagen, Valencia, Calif.). All samples were obtained after informed consent approved by the Harvard Cancer Center/Dana Farber Cancer Institute Institutional Review Board. Quantitative AS-PCR for MYD88-L265P using unselected or CD19-selected cells was performed as described below. The previously established sensitivity and specificity for MYD88 L265P detection by this assay against CD19-selected cells from 104 WM patients and 40 healthy donors was 100% and 92.1%, respectively, with positive predictive and negative predictive values of 95.9% and 100%, respectively, and a ΔCt of <9.6 defining presence of MYD88 L265P.9 Statistical analysis was conducted using Mann Whitney U test. Linear correlation and regression analyses was performed with Spearman's rank correlation. Calculations were performed using R (R Foundation for Statistical Computing Vienna Austria). Fisher's exact probability testing, and estimates of sensitivity, specificity and predictive values were performed using VassarStats.

Allele-specific Polymerase Chain Reaction (AS-PCR)

Two reverse primers were designed to differentiate the mutant and wild-type allele of MYD88 L265P. To optimize the specificity, an internal mismatch in the third position from the 3'-end was introduced. The mutant-specific reverse primer was 5'-CCT TGT ACT TGA TGG GGA aCG-3' (SEQ ID NO: 1) and the wild-type-specific reverse primer was 5'-GCC TTG TAC TTG ATG GGG AaC A-3' (SEQ ID NO: 2). The common forward primer was 5'-AAT GTG TGC CAG GGG TAC TTA G-3' (SEQ ID NO: 3). PCR reaction was performed in a final volume of 25 ul with 50 nM of each primer and 50 ng DNA using PCR SuperMix High Fidelity (Life technology, Calif.). Thermal cycling conditions were: 2 min at 94° C., followed by 40 cycles of 94° C. for 30 s, 57° C. for 30 s, and 68° C. for 30 s, with a final extension at 68° C. for 5 min. The amplified PCR products (159-bp) were separated on 2% agarose gel. To confirm the sequence, PCR products were purified by QIA quick gel extraction kit (Qiagen, Calif.) and sequenced using both forward and reverse PCR primers.

Real-time AS-PCR

Quantitative detection of the MYD88 L265P mutation was developed using the primers described above and Power SYBR® Green PCR Master Mix according to manufacturer's instruction on the ABI Prism 7500 Sequence Detection System (Applied Biosystems, Foster City, Calif.). Briefly, PCR reaction was performed in a final volume of 25 µl with 25 nM of each primer and 50 ng DNA. Thermal cycling conditions were: 10 min at 95° C., followed by 40 cycles of 95° C. for 15 s and 60° C. for 60 s. Each sample was assayed in triplicate. The standard curve for MYD88 L265P was generated by a serial dilution of the mutant DNA with the wild-type DNA (50%, 10%, 2%, 0.4%, 0.08%, and wild-type). For the corresponding reference PCR, the forward primer is same as the one used for the AS-PCR (5'-AAT GTG TGC CAG GGG TAC TTA G-3'; (SEQ ID NO: 3)) and the reverse primer is located at 53-bp downstream of the AS-PCR primer (5'-TGG TGT AGT CGC AGA CAG TGA-3'; (SEQ ID NO: 4)). Levels of the mutant MYD88 L265P in patient samples were calculated based on the value of delta CT and the standard curve.

Results

MYD88 L265P in Unselected PB Cells from WM Patients

The feasibility of using real-time AS-PCR assay to detect MYD88-L265P in peripheral blood (PB) using unselected PB mononuclear cells from 88 untreated WM patients was first determined. Eighty-one (92%) of these patients expressed the MYD88-L265P mutation in CD19-selected B-cells derived from BM aspirations. Of the 81 patients who expressed MYD88-L265P, 32 (40%) were positive for MYD88-L265P using unselected PB mononuclear cells. Taken together, these findings yield a sensitivity of 39.5%, specificity of 100%, positive and negative predictive values of 100% and 12.5%, respectively, for determination of MYD88 L265P by AS-PCR assay using unselected PB mononuclear cells in untreated WM patients.

MYD88 L265P in CD19-selected PB Cells from WM and IgM MGUS Patients

CD19-selected cells from WM patients were isolated with a convenient magnetic based (Dynabead) selection kit. The purity of CD19+ cells isolated with Dynabeads was >80%, and was on par with the yield and purity achieved with Microbeads. By quantitative MYD88 L265P AS-PCR assay, Dynabead CD19-selected PB cells from 118 untreated WM, 102 previously treated WM, 12 IgM MGUS, 3 hyper-IGM, and 1 IgG LPL patients were then analyzed. The median PB MYD88 L265P ΔCt was 3.77, 7.24, 2.47, 10.89, 12.33, and 14.07 in patients with untreated WM, previously treated WM, IgG LPL, IgM MGUS, hyper-IgM syndrome, and healthy donors, respectively (p<0.0001 by ANOVA). Among untreated WM patients, the median PB MYD88 L265P ΔCt was 4.55 and 3.27 for smoldering and symptomatic patients, respectively (p=0.098). Using a MYD88 L265P ΔCt of 9.6, 114/118 (96.6%) untreated WM patients, including 49/51 (96.1%) smoldering and 65/67 (97.0%) symptomatic patients were positive (FIG. 1). The median PB MYD88 L265P ΔCt was 3.58 for all untreated WM patients that were positive for PB MYD88 L265P, and 4.51 and 3.18 for those untreated WM patients with smoldering and symptomatic disease, respectively. MYD88 L265P was detected in CD19-selected PB cells from previously treated WM patients, though a lower fraction of patients, i.e. 63/102 (61.8%) demonstrated positivity (p<0.0001 versus untreated WM patients). The median PB MYD88 L265P ΔCt for positive patients with previously treated disease was 5.05. MYD88 L265P was also detected in a lower fraction of IgM MGUS patients, i.e. 5/12 (41.2%; p<0.0001 versus untreated), as well as in one untreated IgG LPL patient. The median PB MYD88 L265P ΔCt for positive patients with IgM MGUS was 8.22. All 3 hyper-IgM syndrome patients, and 40 healthy donors were negative for MYD88 L265P by AS-PCR examination of PB CD19-selected cells.

Figure 2A:
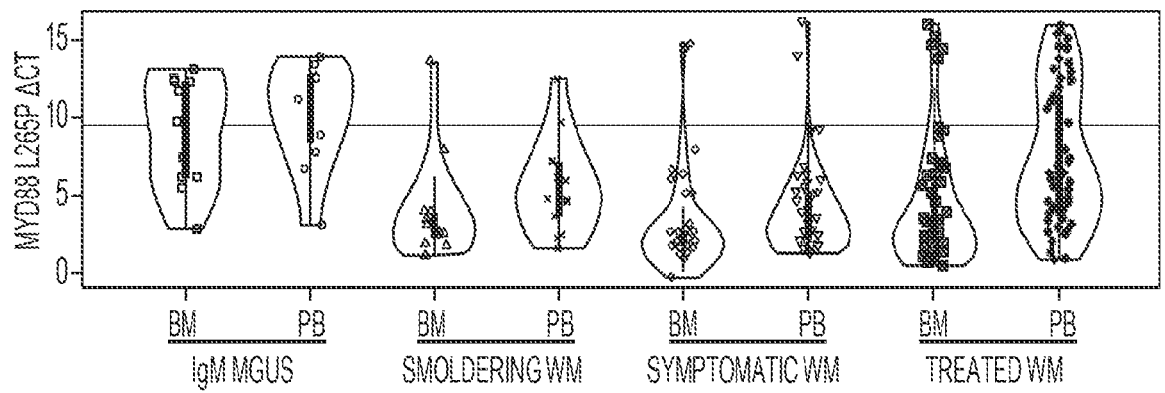
FIG. 2A shows the violin plots representing AS-PCR differences in cycle threshold (ΔCt). The span of grey area for each cohort represents the kernel density estimation of the sample distribution, and highlights the bimodal nature of the data. Box plots with interquartile ranges are shown in black with an overlay of the individual data points. Paired PM and PB samples evaluated were from patients with IgM MGUS (n=12); smoldering WM (n=13); symptomatic WM (n=48); and previously treated WM (n=66). The light grey bar represents the distance between the highest positive, and lowest negative ΔCt values.

MYD88 L265P in Paired CD19-selected BM and PB Cells from WM and IgM MGUS Patients Next paired analysis of CD19-selected samples from the PB and BM in 61 untreated and 66 previously treated WM patients, and 12 IgM MGUS patients was performed (FIG. 2A). The baseline clinical parameters for paired patients did not significantly differ when compared to corresponding patients cohorts that included both paired and unpaired patients (Table 1). Additionally, no significant differences in median prior therapies, time from last therapy, on versus off active therapy and prior treatment with a rituximab containing regimen were observed for paired versus all previously treated patients (data not shown). Analysis of paired BM and PB samples from the untreated WM cohort included 13 smoldering and 48 symptomatic patients. Using a cutoff ΔCt of 9.6, MYD88 L265P was detected in 12 (92.3%) and 46 (95.7%) CD19-selected BM samples from smoldering and symptomatic untreated WM patients, respectively. Among the positive patients, MYD88 L265P was detected in paired PB CD19-selected samples in 11/12 (92%) and 46/46 (100%) of smoldering and symptomatic patients, respectively. Therefore MYD88 L265P was detected in 57/58 (98.3%) of the untreated WM patients by PB AS-PCR examination. For the 1 smoldering patient with negative MYD88 L265P PB results, expression for MYD88 L265P in the corresponding BM sample was weakly positive with a ΔCt close to the cutoff for positivity. The 57 untreated WM patients who were positive for MYD88 L265P by PB examination were also positive by BM examination. Taken together, these findings yield a sensitivity of 98.2%, specificity of 100%, positive and negative predictive values of 100% and 75%, respectively, for determination of MYD88 L265P by AS-PCR assay using Dynabead CD19-selected PB cells in untreated WM patients.

For the 12 individuals with IgM MGUS, MYD88 L265P was present in 6 (50%) and 5 (41.7%) of the BM and PB CD19-selected samples, respectively. All 5 IgM MGUS patients who were positive for MYD88 L265P by PB examination also expressed this mutation by BM examination; therefore MYD88 L265P was detected in 5/6 (83.3%) of these individuals by PB AS-PCR examination. For the 1 IgM MGUS patient with negative MYD88 L265P PB result but who was positive in the BM, expression for the mutation in the corresponding BM sample was weakly positive with a ΔCt close to the cutoff for positivity. The findings yield a sensitivity of 83.3%, specificity of 100%, positive and negative predictive values of 100% and 85.7%, respectively, for determination of MYD88 L265P by AS-PCR assay using Dynabead CD19-selected PB cells in IgM MGUS patients. In comparison to untreated WM patients, fewer IgM MGUS patients were MYD88 L265P positive by either BM or PB examination (p<0.0001).

Next, paired analysis of CD19-selected samples from the BM and PB of 66 previously treated WM patients which included 44 patients off therapy, 22 on continued active therapy including ibrutinib (n=11), everolimus (n=5), rituximab based maintenance (n=5), and chlorambucil (n=1) was performed. Analysis of CD19-selected BM samples from these patients showed expression of MYD88 L265P in 61/66 (92.4%) and 45/66 (68.2%) of BM and PB CD19-selected samples, respectively. There was no significant difference in presence of MYD88 L265P in either BM or PB samples based on "off" versus "on continued active" treatment status, time from prior therapy, number of prior therapies, including prior rituximab treatment. All 45 previously treated WM patients who were positive for MYD88 L265P by PB examination also expressed this mutation by BM examination; therefore MYD88 L265P was detected in 45/61 (73.7%) of these individuals by PB AS-PCR examination. Taken together, these findings yield a sensitivity of 73.7%, specificity of 100%, positive and negative predictive values of 100% and 23.8%, respectively, for determination of MYD88 L265P by AS-PCR assay using Dynabead CD 19+ selected PB cells in previously treated WM patients. Previously treated patients with negative MYD88 L265P PB results but who were positive by BM examination showed lower BM disease burden (p=0.001), lower serum IgM level (p=0.019), and higher hemoglobin levels (p=0.004) versus those patients who displayed MYD88 L265P by PB examination.

BM MYD88 L265P ΔCt and Disease Burden Correlates with PB MYD88 L265P ΔCt in Untreated and Previously Treated WM Patients.

Among all untreated (smoldering and symptomatic) WM and IgM MGUS patients, PB MYD88 L265P ΔCt strongly correlated to BM MYD88 L265P ΔCt (r=0.835; p<0.00001; FIG. 2-B). Restricting the analysis to MYD88 L265P positive patients determined by BM AS-PCR analysis, PB MYD88 L265P ΔCt showed a strong correlation to BM MYD88 L265P ΔCt in untreated WM patients (r=0.700; p<0.00001), untreated WM and IgM MGUS patients combined (r=0.758; p<0.00001), as well as in previously treated WM patients (r=0.588; p<0.00001). We next compared MYD88 L265P ΔCt from BM and PB samples to BM disease involvement, established by histopathological review, as well as serum IgM and hemoglobin levels in patients who were MYD88 L265P positive by BM examination. Both BM (r=−0.354; p=0.006) and PB (r=−0.271; p=0.004) MYD88 L265P ΔCt inversely correlated with BM disease involvement in untreated WM patients. BM (r=−0.486; p<0.0001) and PB (r=−0.400; p=0.001) MYD88 L265P ΔCt also inversely correlated with BM disease involvement when untreated WM and IgM MGUS patients were combined. Both BM (r=−0.269; p=0.031) and PB (r=−0.345; p<0.005) MYD88 L265P ΔCt inversely correlated with absolute lymphocyte count (ALC) in untreated WM and IgM MGUS patients. No significant correlation for either BM or PB MYD88 L265P ΔCt with serum IgM or hemoglobin levels was observed in untreated WM patients, or when untreated WM patients were combined with IgM MGUS patients. Among previously treated patients, both BM (r=−0.604; p<0.0001) and PB (r=−0.442; p=0.0004) MYD88 L265P ΔCt inversely correlated with BM disease involvement. Both BM (r=0.403; p=0.0013) and PB (r=0.500; p<0.0001) MYD88 L265P ΔCt positively also correlated with hemoglobin levels, whereas no significant correlation was observed with either BM or PB MYD88 L265P ΔCt with absolute lymphocyte count or serum IgM levels in previously treated patients.

Comparison of Serum IgM and PB MYD88 L265P ΔCt to Underlying BM Disease Burden in Untreated and Previously Treated WM Patients.

Serum IgM is typically used to monitor MGUS and WM patients for changes in underlying BM disease burden. Therefore, the relative correlations of serum IgM levels and PB MYD88 L265P ΔCt to underlying BM disease burden in untreated and previously treated WM patients were compared, and a Fisher's r to z transformation was calculated to assess the significance of the difference between correlations. Among 112 untreated MGUS and WM patients who were positive for MYD88 L265P by PB AS-PCR examination, and for whom BM pathological assessment was performed, serum IgM (r=0.3375; p=0.0003) and PB MYD88 L265P ΔCt (r=−0.3062; p=0.001) both correlated with BM disease involvement and did not demonstrate any significant difference (p=0.7963) by Fisher's r to z transformation. Similarly, among 74 previously treated WM patients who were positive for MYD88 L265P by PB AS-PCR examination, and for whom BM pathological assessment was performed, serum IgM (r=0.3296; p=0.0041) and PB MYD88 L265P ΔCt (r=−0.4457; p<0.0001) both correlated with BM disease involvement and also did not demonstrate any significant difference (p=0.4146) by Fisher's r to z transformation.

PB MYD88 L265P ΔCt can Distinguish WM from IgM MGUS Patients

Figure 2B:
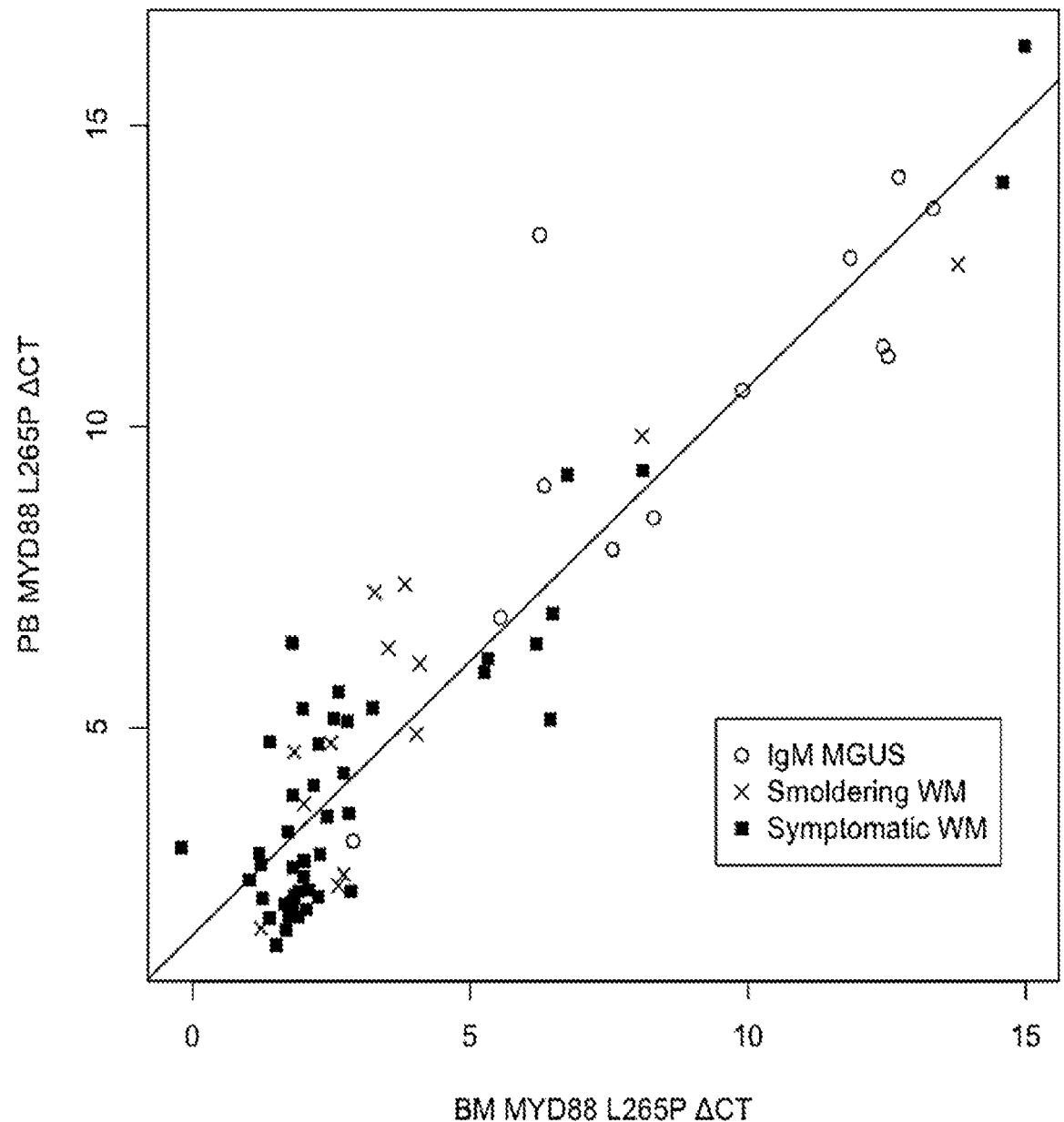
FIG. 2B shows the correlation of real-time AS-PCR results for paired BM and PB MYD88 L265P ΔCt in untreated patients with IgM MGUS, smoldering and symptomatic WM.

Both IgM MGUS and WM patients can exhibit the MYD88 L265P mutation by PB AS-PCR examination (FIGS. 1, 2A), and PB MYD88 L265P ΔCt showed a strong correlation to underlying BM disease involvement (FIG. 2B). Next, it was determined if PB MYD88 L265P ΔCt could discriminate IgM MGUS from untreated WM patients. PB MYD88 L265P ΔCt levels was examined in the 64 paired patients with untreated WM which included 12 smoldering and 46 symptomatic patients, along with 6 IgM MGUS patients whose positive MYD88 L265P status was established by BM examination. The median PB MYD88 L265P ΔCt for positive IgM MGUS, smoldering WM, and symptomatic untreated WM patients was 8.22, 4.83, and 2.91, respectively (p<0.0001 by ANOVA). Fifty-two of 58 (90%) of the patients with a PB MYD88 L265P ΔCt of 6.5 or lower had the diagnosis of WM, including 9/12 (75%) smoldering and 43/46 (94%) symptomatic untreated WM patients. In contrast, none of the 6 patients with IgM MGUS had a PB MYD88 L265P ΔCt of 6.5 or lower (p<0.0001). The PB MYD88 L265P ΔCt cutoff of 6.5 was then applied to the entire untreated WM and IgM MGUS cohort whose positive MYD88 L265P status was determined by PB examination. This cohort included 119 untreated patients, inclusive of 49 smoldering and 65 symptomatic WM patients, and 5 patients with IgM MGUS. The median PB MYD88 L265P ΔCt for positive IgM MGUS, smoldering WM, and symptomatic untreated WM patients was 7.96, 4.46, and 3.08, respectively (p<0.0001 by ANOVA). One-hundred and one of 119 (85%) of the patients with a PB MYD88 L265P ΔCt of 6.5 or lower had the diagnosis of WM, including 40/49 (82%) smoldering and 43/46 (94%) symptomatic untreated WM patients. In contrast, none of the 5 patients with IgM MGUS had a PB MYD88 L265P ΔCt of 6.5 or lower (p<0.0001).

A highly sensitive and specific AS-PCR assay was used for determining MYD88 L265P status in BM CD19-selected cells. Initially, unselected PB cells from untreated WM patients were examined. The low sensitivity (39.5%) for detecting MYD88 L265P by this method prompted examination of the use of CD19-selected PB cells by Dynabead isolation for AS-PCR testing. Dynabeads represent a convenient and affordable means for CD19 selection, which may easily be adoptable for use in clinical pathology laboratories where flow based sorting is time and cost prohibitive. By use of Dynabead isolation, it was demonstrated that PB MYD88 L265P testing was associated with high rates of sensitivity (98.1%) and specificity (100%) in untreated WM patients. A high level of sensitivity for PB MYD88 L265P testing was also present in IgM MGUS patients (83.3%). These findings contributed to high positive and negative predictor values for determining MYD88 L265P status in untreated WM and IgM MGUS patients, though a few patients who were negative by examination of PB CD 19-selected cells were positive by BM examination. These findings suggest that for the majority of untreated WM and IgM MGUS patients, AS-PCR examination of CD 19-selected PB samples should be able to determine MYD88 L265P status, though in some patients whose findings are negative, a bone marrow biopsy could be considered for establishing mutation status. In contrast to the high sensitivity for PB MYD88 L265P testing observed in untreated patients, MYD88 L265P detection in previously treated patients was associated with a lower sensitivity of 73.7%, and a negative predictive value of 23.8%. The specificity (100%) and positive predictive value (100%) in previously treated patients remained high, and coincided with values observed in untreated patients. These findings affirm that while MYD88 L265P is likely to be detected by AS-PCR in most previously treated patients, absence of its recognition by PB CD19-selected examination should not be taken to reflect a negative finding and BM examination should also be considered in these patients to establish mutation status. By use of AS-PCR, most untreated WM (96.6%), previously treated (61.8%) WM, and IgM MGUS (83.3%) were positive for MYD88 L265P in these studies. It is interesting, that one IgG LPL patient was also positive by PB examination. In previous studies, 3 of 3 non-IgM LPL patients were MYD88 L265P positive by BM examination.

The above findings confirm that peripheral blood AS-PCR testing for MYD88 L265P may in the appropriate clinical context be used to establish the diagnosis of WM. Appropriate clinical context could include demonstration of cytopenias in the absence of other medical etiologies, and/or presence of morbidities attributable to WM such as hyperviscosity, adenopathy or splenomegaly in the presence of elevated serum IgM levels and the presence of an IgM monoclonal protein. Use of PB MYD88 L265P ΔCt, as demonstrated herein, could also help distinguish WM from IgM MGUS patients who are typically asymptomatic, have low serum IgM levels, and lack cytopenias and/or extramedullary disease. In patients that are negative by PB AS-PCR testing for MYD88 L265P, a BM biopsy may then be considered in order to clarify the underlying diagnosis. Similar molecular based testing has obviated the need for routine bone marrow examination in patients with other hematological conditions including chronic myelogenous leukemia (BCR-ABL), polycythemia vera (JAK2 V617F) and hairy cell leukemia (BRAF V600E).25-27 The use of PB MYD88 L265P testing for establishing the diagnosis of WM could potentially save time, reduce costs, and alleviate pain and patient anxiety associated with a BM biopsy.

It is interesting that the absence of PB MYD88 L265P expression in previously treated patients was associated with lower, but detectable levels of BM disease burden. From a biological point of view, the absence of PB circulating disease in these patients is intriguing, and consistent with prior studies that found decreased circulating disease in responding patients. These findings may be indicative of tumor cell sparing in BM relative to the peripheral circulation that may be afforded by a protective microenvironment. The application of PB MYD88 L265P testing, including serial assessment of MYD88 L265P ΔCt values in patients undergoing therapy could be useful in assessing not only treatment response, but also the differential impact of treatment on PB and BM compartments. The use of BM MYD88 L265P ΔCt to assess changes in BM tumor burden following therapy has previously been demonstrated, and the high degree of correlation between PB and BM MYD88 L265P ΔCt as shown in these studies supports the investigation of PB MYD88 L265P ΔCt in prospective therapeutic trials.

The recognition that serum IgM and PB MYD88 L265P ΔCt values showed similar strengths of correlation with underlying disease burden is also noteworthy. Frequent discordance between serum IgM and underlying BM disease has frequently been reported with agents used in the treatment of WM including rituximab, bortezomib, everolimus, and ibrutinib. Rituximab induces an IgM flare in about half of WM patients, which is more pronounced with concurrent administration of an immunomodulatory agent. Increased serum IgM can be mistaken for disease progression leading to change in drug therapy. Conversely, bortezomib, everolimus and ibrutinib can block IgM secretion out of proportion to tumor load, therefore lending to underestimations of post-treatment disease burden, and in some instances missing WM disease progression. The use of PB MYD88 L265P ΔCt to estimate underlying disease burden in patients undergoing treatments which differentially affect serum IgM levels can help guide clinical management, and avoid repetition of BM biopsies to clarify IgM discordance as is the current standard of care.

In summary, the feasibility of detecting MYD88 L265P by use of PB AS-PCR testing, with high rates of sensitivity and specificity particularly for untreated WM and IgM MGUS patients has been confirmed. In the appropriate clinical context, and supported by PB MYD88 L265P ΔCt, the use of PB MYD88 L265P testing provides a convenient, non-invasive, and inexpensive method to establish the diagnosis of WM, and follow changes in underlying disease burden.

REFERENCES

1. Owen R G, Treon S P, Al-Katib A, Fonseca R, Greipp P R, McMaster M L, Morra E, Pangalis G A, San Miguel J F, Branagan A R, Dimopoulos M A. Clinicopathological definition of Waldenstrom's macroglobulinemia: Consensus panel recommendations from the Second International Workshop on Waldenstrom's Macroglobulinemia. Semin Oncol. 2003; 30(2):110-115.
2. Swerdlow S, Campo, E, Harris, N L, et al. (eds.): World Health Organization Classification of Tumours of Haematopoietic and Lymphoid Tissues (ed 4th). Lyon, France, IARC Press, 2008.
3. Treon S P. How I treat Waldenström macroglobulinemia. Blood 2009; 17; 114(12):2375-85.
4. Smith B R, Robert N J, Ault K A. In Waldenstrom's macroglobulinemia the quantity of detectable circulating monoclonal B lymphocytes correlates with clinical course. Blood 1983; May; 61(5):911-4.
5. Kriangkum J, Taylor B J, Treon S P, et al. Clonotypic IgM V/D/J sequence analysis in Waldenstrom macroglobulinemia suggests an unusual B-cell origin and an expansion of polyclonal B cells in peripheral blood. Blood 2004; October 1; 104(7):2134-42.
6. Ngo V N, Young R M, Schmitz R, et al. Oncogenically active MYD88 mutations in human lymphoma, Nature, 3; 470(7332):115-9, 2011.
7. Treon S P, Xu L, Yang G, et al: MYD88 L265P somatic mutation in Waldenstrom's macroglobulinemia. N Engl J Med 2012; 367:826-33.
8. Treon S P, Hunter Z R. MYD88 L265P Somatic Mutation in IgM MGUS. New England Journal of Medicine 2012; 367:2256-2257.
9. Xu L, Hunter Z R, Yang G, et al: MYD88 L265P in Waldenstrom macroglobulinemia, immunoglobulin M monoclonal gammopathy, and other B-cell lymphoproliferative disorders using conventional and quantitative allele-specific polymerase chain reaction. Blood 2013; 121:2051-8.
10. Landgren O, Staudt L: MYD88 L265P somatic mutation in IgM MGUS. N Engl J Med 2012; 367:2255-6.
11. Gachard N, Parrens M, Soubeyran I, et al. IGHV gene features and MYD88 L265P mutation separate the three marginal zone lymphoma entities and Waldenstrom macroglobulinemia/lymphoplasmacytic lymphomas. Leukemia. 2013; 27:183-9.
12. Varettoni M, Arcaini L, Zibellini S, et al: Prevalence and clinical significance of the MYD88 (L265P) somatic mutation in Waldenstrom's macroglobulinemia and related lymphoid neoplasms. Blood 2013; 121:2522-8.
13. Jimenez C, Sebastian E, Del Carmen Chillon M, et al: MYD88 L265P is a marker highly characteristic of, but not restricted to, Waldenstrom's macroglobulinemia. Leukemia 2013; August; 27(8):1722-8.
14. Poulain S, Roumier C, Decambron A, et al. MYD88 L265P mutation in Waldenstrom's macroglobulinemia. Blood 2013; May 30; 121(22):4504-11.
15. Willenbacher W, Willenbacher E, Brunner A, et al: Improved accuracy of discrimination between IgM Multiple Myeloma and Waldenstrom Macroglobulinaemia by testing for MYD88 L265P mutations. Br J Haematol 2013; Br J Haematol. 2013 June; 161(6):902-4.
16. Ondrejka S L, Lin J J, Warden D W, et al. MYD88 L265P somatic mutation: its usefulness in the differential diagnosis of bone marrow involvement by B-cell lymphoproliferative disorders. Am J Clin Pathol. 2013 September; 140(3):387-94.
17. Argentou N, Vassilopoulos G, Ioannou M, et al. Rapid detection of MYD88-L265P mutation by PCR-RFLP in B-cell lymphoproliferative disorders. Leukemia. 2013 Oct. 18. doi: 10.1038/1eu.2013.294.
18. Puente X S, Pinyol M, Quesada V, et al. Whole-genome sequencing identifies recurrent mutations in chronic lymphocytic leukaemia. Nature. 2011; 475(7354):101-105.
19. Watters T, Kenny E F, O'Neill L A J. Structure, function and regulation of the Toll/IL-1 receptor adaptor proteins. Immunol Cell Biol. 2007; 85(6): 411-419.
20. Loiarro M, Gallo G, Fantò N, De Santis R, Carminati P, Ruggiero V, Sette C. Identification of critical residues of the MYD88 death domain involved in the recruitment of downstream kinases. J Biol Chem. 2009; 284(41): 28093-281023.
21. Lin S C, Lo Y C, Wu H. Helical assembly in the MYD88-IRAK4-IRAK2 complex in TLR/IL-1R signaling. Nature. 2010; 465(7300): 885-891.
22. Yang G, Zhou Y, Liu X, et al. A mutation in MYD88 (L265P) supports the survival of lymphoplasmacytic cells by activation of Bruton tyrosine kinase in Waldenstrom macroglobulinemia. Blood. 2013; 122(7):1222-32.
23. Treon S P, Tripsas C, Yang G, et al. A Prospective Multicenter Study Of The Bruton's Tyrosine Kinase Inhibitor Ibrutinib In Patients With Relapsed Or Refractory Waldenstrom's Macroglobulinemia. Proc. of the American Society of Hematology. Blood 2013; Abstract 251.
24. Kyle R A, Treon S P, Alexanian R, et al. Prognostic markers and criteria to initiate therapy in Waldenstrom's Macroglobulinemia: Consensus Panel Recommendations from the Second International Workshop on Waldenstrom's Macroglobulinemia. Semin Oncol 2003; 30: 116-120.

25. Kiss T L, Xu W M, Jamal N, Messner H A. Comparative testing of peripheral blood and bone marrow for BCR-ABL transcripts in patients post allogeneic bone marrow transplantation and during interferon treatment for chronic myeloid leukemia. Leuk Lymphoma. 1999 August; 34(5-6):493-500.
26. Passamonti F. How I treat polycythemia vera. Blood 2012; July 12; 120 (2): 275-84.
27. Tiacci E, Schiavoni G, Forconi F, et al. Simple genetic diagnosis of hairy cell leukemia by sensitive detection of the BRAF-V600E mutation. Blood 2012; 119:192-195.
28. Ngo H T, Leleu X, Lee J, Jia X, Melhem M, Runnels J, Moreau A S, Burwick N, Azab A K, Roccaro A, Azab F, Sacco A, Farag M, Sackstein R, Ghobrial I M. SDF-1/CXCR4 and VLA-4 interaction regulates homing in Waldenstrom macroglobulinemia. Blood. 2008 Jul. 1; 112(1):150-8.
29. Hodge L S, Ziesmer S C, Yang Z Z, et al. IL-21 in the bone marrow microenvironment contributes to IgM secretion and proliferation of malignant cells in Waldenstrom macroglobulinemia. Blood. 2012 Nov. 1; 120(18):3774-82.
30. Treon S P, Hunter Z R, Matous J, et al. Multicenter Clinical Trial of Bortezomib in Relapsed/Refractory Waldenstrom's Macroglobulinemia: Results of WMCTG Trial 03-248. Clin Cancer Res 2007; 13:3320-5.
31. Treon S P, Tripsas C K, Ioakimidis L, et al. Prospective, Multicenter Study of the Mtor Inhibitor Everolimus (RAD001) As Primary Therapy in Waldenstrom's Macroglobulinemia. Blood 2011; 118: 2951.
32. Anderson K C, Alsina M, Bensinger W, et al. Multiple Myeloma, version 1.2013. J Natl Compr Canc Netw. 2013 Jan. 1; 11(1):11-7.

TABLE 1

Baseline characteristics of patients with WM and IgM MGUS. Median values provided. p-values denote significance by ANOVA for comparisons within WM and IgM MGUS cohorts for all patients, and for BM and PB paired patients.

|  | N | Gender | Age | BM | WBC | HGB | HCT | PLT | ANEUT | ALYMP | IgG | IgA | IgM |
|---|---|---|---|---|---|---|---|---|---|---|---|---|---|
| All patients | | | | | | | | | | | | | |
| IgM MGUS | 12 | 6M/6F | 62.5 | 0 | 5.45 | 13.35 | 38.35 | 248.5 | 3.78 | 1.25 | 937 | 139.5 | 437 |
| Smoldering WM | 51 | 31M/20F | 61 | 20 | 7.2 | 13 | 38 | 247 | 4.43 | 1.78 | 658.5 | 72 | 1900 |
| Symptomatic WM | 67 | 33M/34F | 60 | 50 | 6 | 11.4 | 33 | 247 | 3.53 | 1.7 | 639.5 | 52 | 3320 |
| Treated WM | 102 | 72M/30F | 57.5 | 40 | 5.3 | 11.8 | 34.8 | 205 | 3.175 | 1.04 | 402 | 27 | 1700 |
| ANOVA p-value | | | 0.611 | <0.0001 | 0.0006 | <0.0001 | <0.0001 | 0.0282 | 0.0016 | 0.225 | <0.0001 | <0.0001 | <0.0001 |
| Paired patients | | | | | | | | | | | | | |
| IgM MGUS | 12 | 6M/6F | 62.5 | 0 | 5.45 | 13.35 | 38.35 | 248.5 | 3.78 | 1.25 | 937 | 139.5 | 437 |
| Smoldering WM | 13 | 9M/4F | 63 | 15 | 6.9 | 12.4 | 37.1 | 208 | 3.655 | 1.89 | 651 | 81 | 1240 |
| Symptomatic WM | 48 | 24M/24F | 58.5 | 50 | 6.3 | 11.45 | 33 | 253 | 3.71 | 1.73 | 610 | 53 | 3285 |
| Treated WM | 66 | 49M/17F | 56 | 32.5 | 5.35 | 11.95 | 35 | 216 | 2.97 | 1.035 | 353.5 | 26 | 1540 |
| ANOVA p-value | | | 0.213 | <0.0001 | 0.0513 | 0.0006 | 0.0015 | 0.0456 | 0.126 | <0.0001 | 0.0062 | <0.0001 | 0.0007 |

We claim:

1. A method to distinguish Waldenström's Macroglobulinemia from IgM monoclonal gammopathy of undetermined significance in a subject, the method comprising:
obtaining a biological sample from a subject in need thereof,
determining a level of a transcript comprising a mutation at position 38182641 in chromosome 3p22.2 in the biological sample by performing an allele-specific polymerase chain reaction assay to generate a delta $C_T$ value, wherein the allele specific polymerase chain reaction assay is performed using an allele specific primer, wherein the allele specific primer hybridizes at or near its 3' end to the mutation at position 38182641 in chromosome 3p22.2, and
diagnosing the subject as more likely to have Waldenström's Macroglobulinemia than IgM monoclonal gammopathy of undetermined significance if the delta $C_T$ value is less than a reference value or diagnosing the subject as more likely to have IgM monoclonal gammopathy of undetermined significance than Waldenström's Macroglobulinemia if the delta $C_T$ value is equal to or greater than the reference value,
wherein the biological sample is a sample of blood, and
wherein the reference value is a reference value such that 95% of subjects with Waldenström's Macroglobulinemia have a delta $C_T$ value that is less than the reference value.

2. The method of claim 1, wherein the mutation results in a single nucleotide change from T to C in the myeloid differentiation primary response 88 (MYD88) gene.

3. The method of claim 1, wherein the mutation results in an amino acid change from leucine to proline at position 265 in the myeloid differentiation primary response 88 protein.

4. The method of claim 1, wherein the allele specific primer is SEQ ID NO: 1.

5. A method to treat Waldenström's Macroglobulinemia in a subject, the method comprising:
administering to a subject in need thereof a therapeutic agent in an amount effective to treat Waldenström's Macroglobulinemia,
wherein the subject has a delta $C_T$ value that is less than a reference value,
wherein the delta $C_T$ value is generated by performing an allele-specific polymerase chain reaction assay to determine a level of a transcript comprising a mutation at position 38182641 in chromosome 3p22.2 in a biological sample obtained from the subject,
wherein the biological sample is a sample of blood,
wherein the reference value is a reference value such that 95% of subjects with Waldenström's Macroglobulinemia have a delta $C_T$ value that is less than the reference value, and
wherein the therapeutic agent is a MYD88 inhibitor, an interleukin receptor associate kinase 1/4 (IRAK-1/4) inhibitor, a phosphoinositide 3-kinase (PI3K) inhibitor and/or a Bruton's tyrosine kinase (BTK) inhibitor.

6. The method of claim 5, wherein the mutation results in a single nucleotide change from T to C in the myeloid differentiation primary response 88 (MYD88) gene.

7. The method of claim 5, wherein the mutation results in an amino acid change from leucine to proline at position 265 in the myeloid differentiation primary response 88 protein.

8. The method of claim 5, wherein the therapeutic agent is a Bruton's tyrosine kinase (BTK) inhibitor.

9. The method of claim 5, wherein the MYD88 inhibitor is a peptidomimetic compound ST2825.

10. The method of claim 5, wherein the IRAK-1/4 inhibitor is N-(2-Morpholinylethyl)-2-(3-nitrobenzoylamido)-benzimidazole.

11. The method of claim 8, wherein the BTK inhibitor is Ibrutinib (PCI-32765).

12. A method to distinguish Waldenström's Macroglobulinemia from IgM monoclonal gammopathy of undetermined significance, the method comprising:
selecting a subject on the basis that the subject presents one or more clinical features of WM and/or IgM MGUS,
obtaining a biological sample from the subject,
determining a level of a transcript comprising a mutation at position 38182641 in chromosome 3p22.2 in the biological sample by performing an allele-specific polymerase chain reaction assay to generate a delta $C_T$ value, wherein the allele specific polymerase chain reaction assay is performed using an allele specific primer, wherein the allele specific primer hybridizes at or near its 3' end to the mutation at position 38182641 in chromosome 3p22.2, and
diagnosing the subject as more likely to have Waldenström's Macroglobulinemia than IgM monoclonal gammopathy of undetermined significance if the delta $C_T$ value is less than a reference value or diagnosing the subject as more likely to have IgM monoclonal gammopathy of undetermined significance than Waldenström's Macroglobulinemia if the delta $C_T$ value is equal to or greater than a reference value, wherein the biological sample is a sample of blood, and wherein the reference value is a reference value such that 95% of subjects with Waldenström's Macroglobulinemia have a delta $C_T$ value that is less than the reference value.

13. A method to distinguish Waldenström's Macroglobulinemia from IgM monoclonal gammopathy of undetermined significance, the method comprising:

performing an assay to determine if the subject has an abnormal level of immunoglobulin M (IgM) in a first biological sample obtained from a subject, and determining a level of a transcript comprising a mutation at position 38182641 in chromosome 3p22.2 in a second biological sample by performing an allele-specific polymerase chain reaction assay obtained from a subject to generate a delta $C_T$ value, wherein the allele specific polymerase chain reaction assay is performed using an allele specific primer, wherein the allele specific primer hybridizes at or near its 3' end to the mutation at position 38182641 in chromosome 3p22.2, and diagnosing the subject as more likely to have Waldenström's Macroglobulinemia than IgM monoclonal gammopathy of undetermined significance if the subject has an abnormal level of IgM and delta $C_T$ value of the biological sample is less than a reference value or diagnosing the subject as more likely to have IgM monoclonal gammopathy of undetermined significance than Waldenström's Macroglobulinemia if the subject has an abnormal level of IgM and delta $C_T$ value of the biological sample is equal to or greater than a reference value, wherein the second biological sample is a sample of blood, and wherein the reference value is a reference value such that 95% of subjects with Waldenström's Macroglobulinemia have a delta $C_T$ value that is less than the reference value.

14. The method of claim 13, wherein the first biological sample used to determine if the subject has an abnormal level of IgM is a sample of blood, urine, bone marrow, lymph node, or spleen.

15. A method comprising:

performing a first assay on a first biological sample obtained from a subject that presents one or more clinical features of Waldenström's Macroglobulinemia (WM) and/or IgM monoclonal gammopathy of undetermined significance (IgM MGUS) to determine if the subject has an abnormal level of immunoglobulin M (IgM);

determining if the subject has an abnormal level of immunoglobulin M (IgM) based on the first assay;

determining a level of a transcript comprising a mutation at position 38182641 in chromosome 3p22.2 in a second biological sample obtained from the subject by performing an allele-specific polymerase chain reaction assay to generate a delta $C_T$ value, wherein the allele specific polymerase chain reaction assay is performed using an allele specific primer, wherein the allele specific primer hybridizes at or near its 3' end to the mutation at position 38182641 in chromosome 3p22.2; and determining the level of a transcript comprising a mutation at position 38182641 in chromosome 3p22.2 based on a comparison of a delta $C_T$ value from the AS-PCR assay to a reference value, wherein the second biological sample is a sample of blood, and wherein the reference value is a reference value such that 95% of subjects with Waldenström's Macroglobulinemia have a delta $C_T$ value that is less than the reference value.

\* \* \* \* \*

SEQUENCE LISTING

<160> NUMBER OF SEQ ID NOS: 4

<210> SEQ ID NO 1
<211> LENGTH: 21
<212> TYPE: DNA
<213> ORGANISM: Artificial Sequence
<220> FEATURE:
<223> OTHER INFORMATION: Synthetic Polynucleotide

<400> SEQUENCE: 1
ccttgtactt gatggggaac g                                         21

<210> SEQ ID NO 2
<211> LENGTH: 22
<212> TYPE: DNA
<213> ORGANISM: Artificial Sequence
<220> FEATURE:
<223> OTHER INFORMATION: Synthetic Polynucleotide

<400> SEQUENCE: 2
gccttgtact tgatggggaa ca                                        22

```
<210> SEQ ID NO 3
<211> LENGTH: 22
<212> TYPE: DNA
<213> ORGANISM: Artificial Sequence
<220> FEATURE:
<223> OTHER INFORMATION: Synthetic Polynucleotide

<400> SEQUENCE: 3
aatgtgtgcc aggggtactt ag                                              22

<210> SEQ ID NO 4
<211> LENGTH: 21
<212> TYPE: DNA
<213> ORGANISM: Artificial Sequence
<220> FEATURE:
<223> OTHER INFORMATION: Synthetic Polynucleotide

<400> SEQUENCE: 4
tggtgtagtc gcagacagtg a                                               21
```